(12) United States Patent
Tojo

(10) Patent No.: US 11,696,675 B2
(45) Date of Patent: Jul. 11, 2023

(54) INSERTION SUPPORT SYSTEM AND INSERTION SUPPORT METHOD

(71) Applicant: OLYMPUS CORPORATION, Tokyo (JP)

(72) Inventor: Ryo Tojo, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 826 days.

(21) Appl. No.: 16/703,978

(22) Filed: Dec. 5, 2019

(65) Prior Publication Data

US 2020/0107705 A1   Apr. 9, 2020

Related U.S. Application Data

(63) Continuation of application No. PCT/JP2017/021625, filed on Jun. 12, 2017.

(51) Int. Cl.

| | |
|---|---|
| *A61B 1/00* | (2006.01) |
| *A61B 1/005* | (2006.01) |
| *A61B 34/20* | (2016.01) |
| *A61B 1/31* | (2006.01) |

(Continued)

(52) U.S. Cl.
CPC .......... *A61B 1/00158* (2013.01); *A61B 1/009* (2022.02); *A61B 1/31* (2013.01);
(Continued)

(58) Field of Classification Search
CPC ..... A61B 1/009; A61B 1/00158; A61B 34/20; A61B 2034/2059
See application file for complete search history.

(56) References Cited

U.S. PATENT DOCUMENTS

2011/0275896 A1* 11/2011 Tanaka ................... A61B 5/064
                                                               600/118
2015/0216391 A1   8/2015 Fujita et al.
(Continued)

FOREIGN PATENT DOCUMENTS

| CN | 104755005 A | 7/2015 |
|---|---|---|
| JP | S59-7919 A | 1/1984 |

(Continued)

OTHER PUBLICATIONS

Chinese Office Action dated Jun. 18, 2021 received in 201780091957.3.

(Continued)

*Primary Examiner* — Anh Tuan T Nguyen
*Assistant Examiner* — Rynae E Boler
(74) *Attorney, Agent, or Firm* — Scully, Scott, Murphy & Presser, P.C.

(57) ABSTRACT

An insertion support system includes a state acquisition apparatus configured to acquire first information. The first information includes at least one of: a plurality of pieces of position information related to a plurality of positions of an insertion section to be inserted into an insertion target body; and a plurality of pieces of direction vector information in a longitudinal axis direction of the insertion section. The insertion support system also includes a support information calculator configured to calculate second information related to a rotation quantity of the insertion section based on the first information, and an output section configured to output the second information.

10 Claims, 17 Drawing Sheets

(51) Int. Cl.
*A61B 5/06* (2006.01)
*A61B 34/00* (2016.01)
*A61B 34/30* (2016.01)

(52) U.S. Cl.
CPC .............. *A61B 5/062* (2013.01); *A61B 34/20* (2016.02); *A61B 34/30* (2016.02); *A61B 34/70* (2016.02); *A61B 2034/2059* (2016.02); *A61B 2034/2072* (2016.02)

(56) References Cited

U.S. PATENT DOCUMENTS

2017/0143191 A1  5/2017  Haraguchi et al.
2018/0125591 A1* 5/2018  Camarillo .............. A61B 34/71

FOREIGN PATENT DOCUMENTS

| JP | H11-281897 A | 10/1999 |
|---|---|---|
| JP | 2000-175861 A | 6/2000 |
| JP | 2012-100885 A | 5/2012 |
| JP | 2014-79376 A | 5/2014 |

OTHER PUBLICATIONS

International Search Report dated Sep. 5, 2017 issued in PCT/JP2017/021625.
English translation of International Preliminary Report on Patentability dated Dec. 26, 2019, together with the Written Opinion received in related International Application No. PCT/JP2017/021625.

* cited by examiner

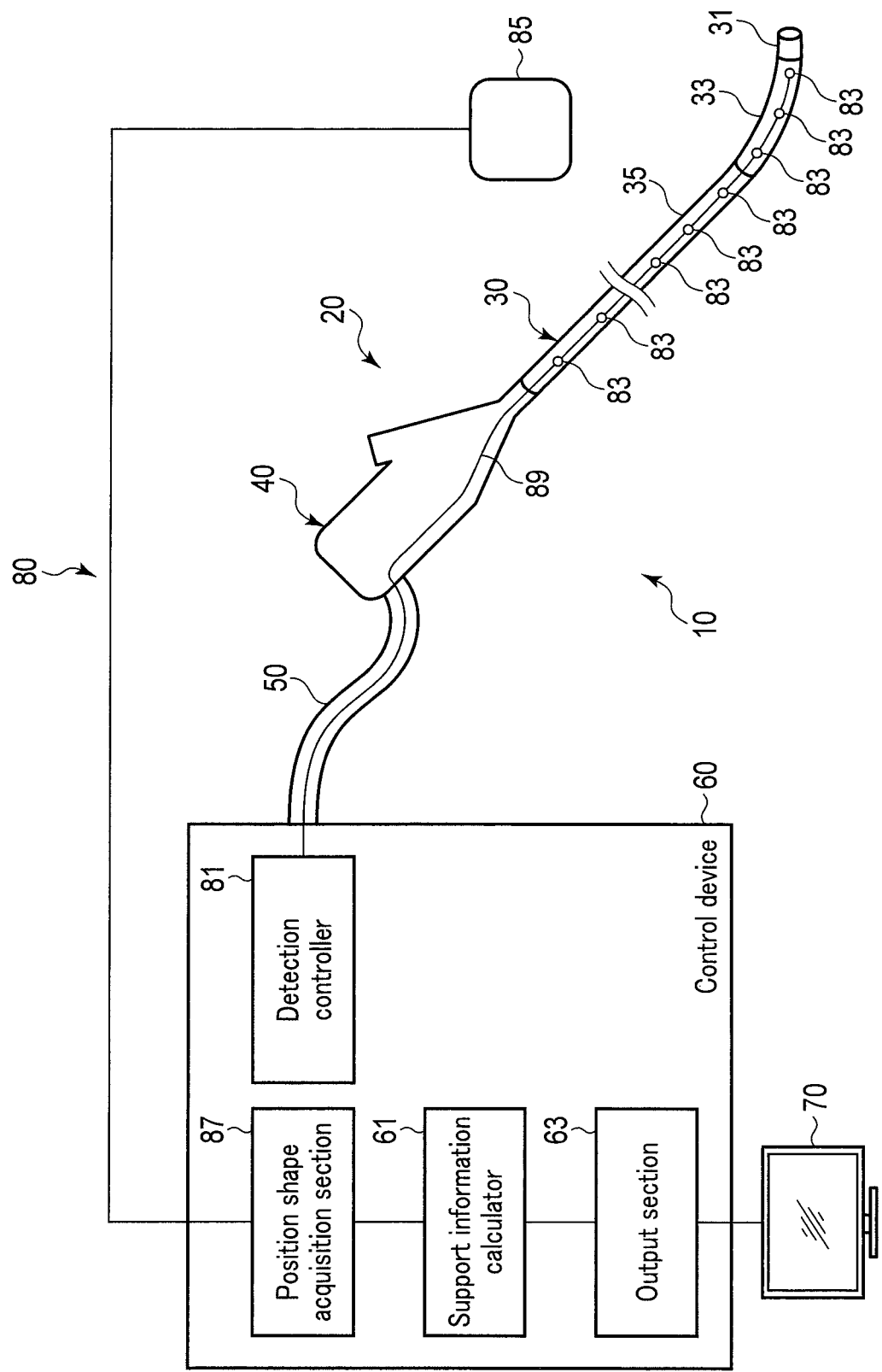
F I G. 1

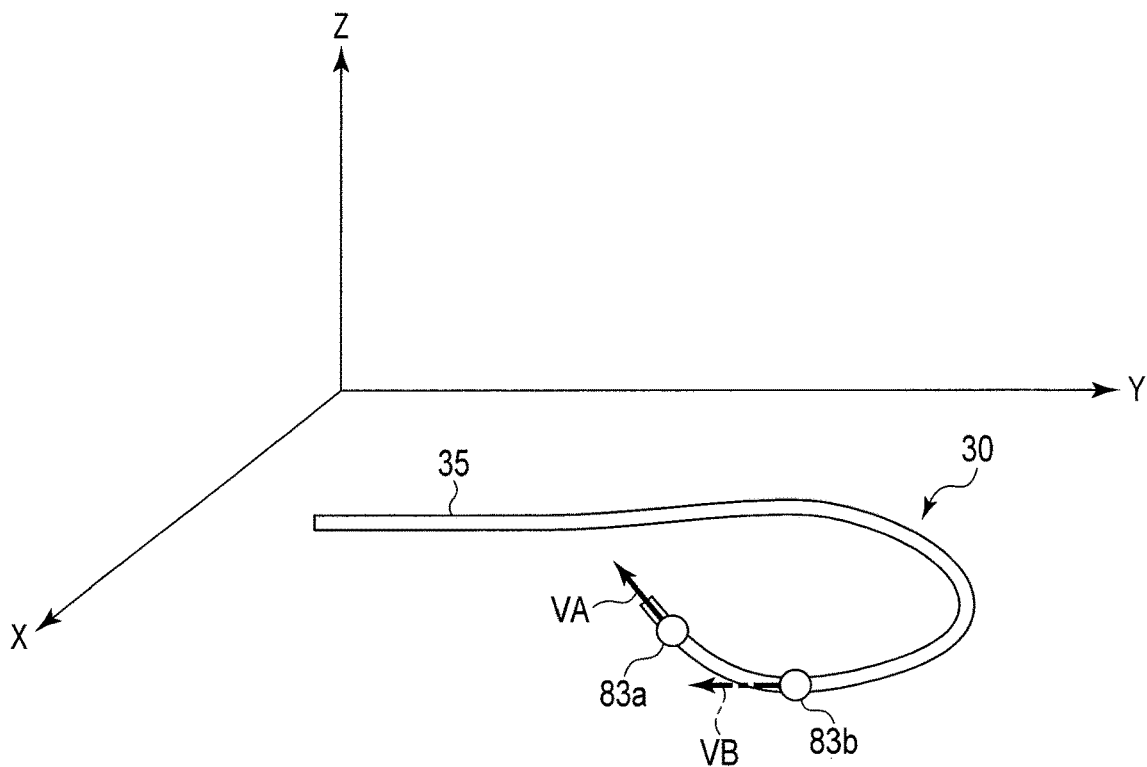
F I G. 4A
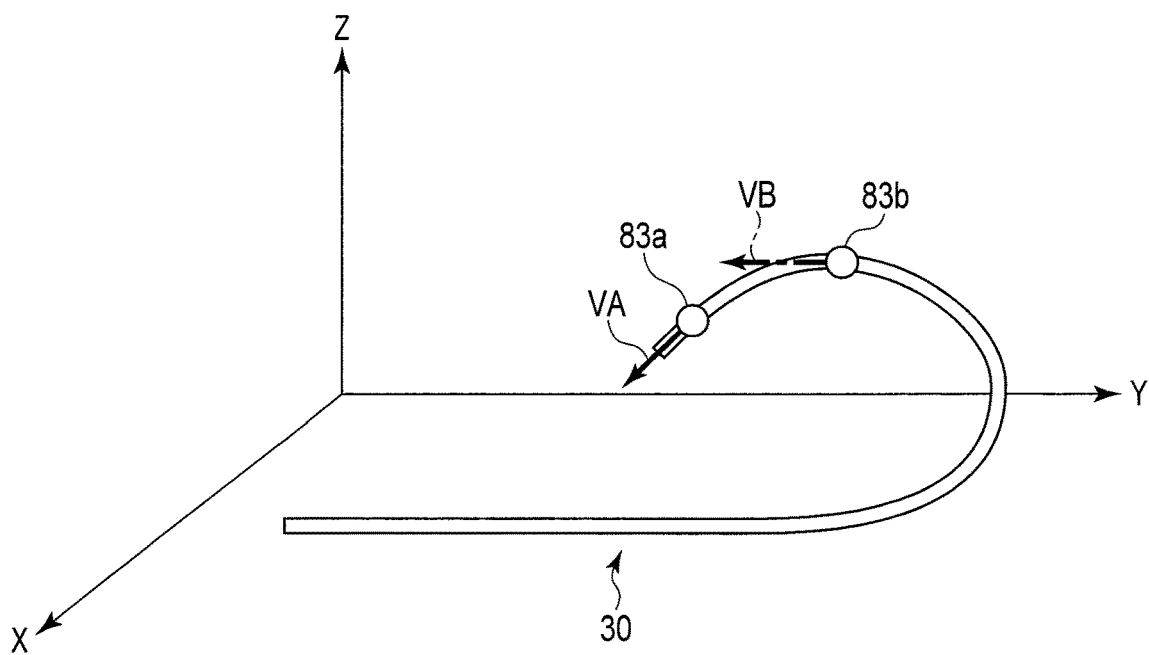
F I G. 4B

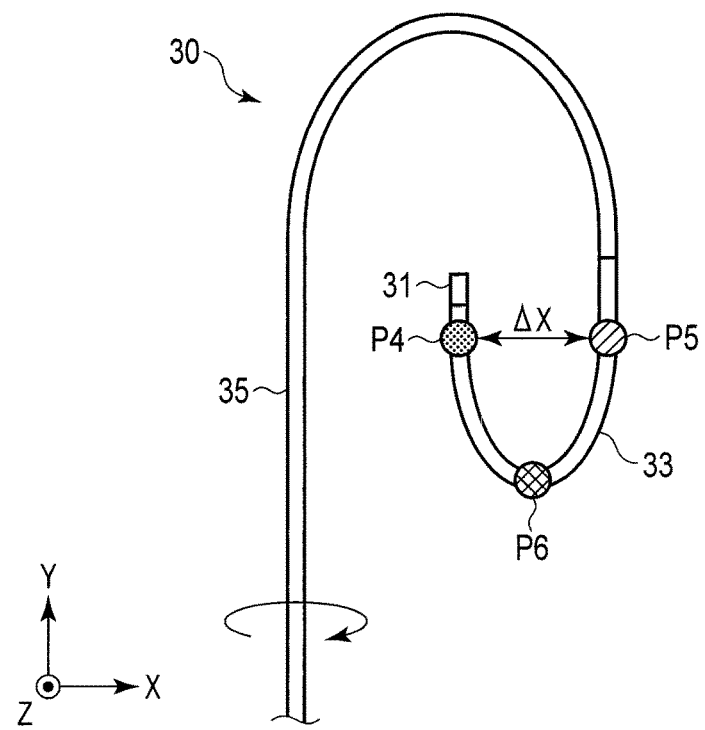
F I G. 11A
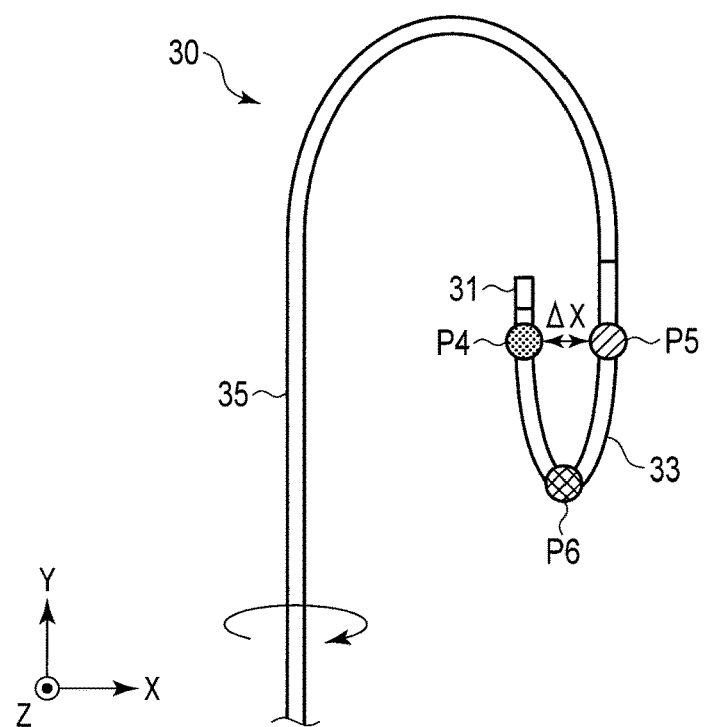
F I G. 11B

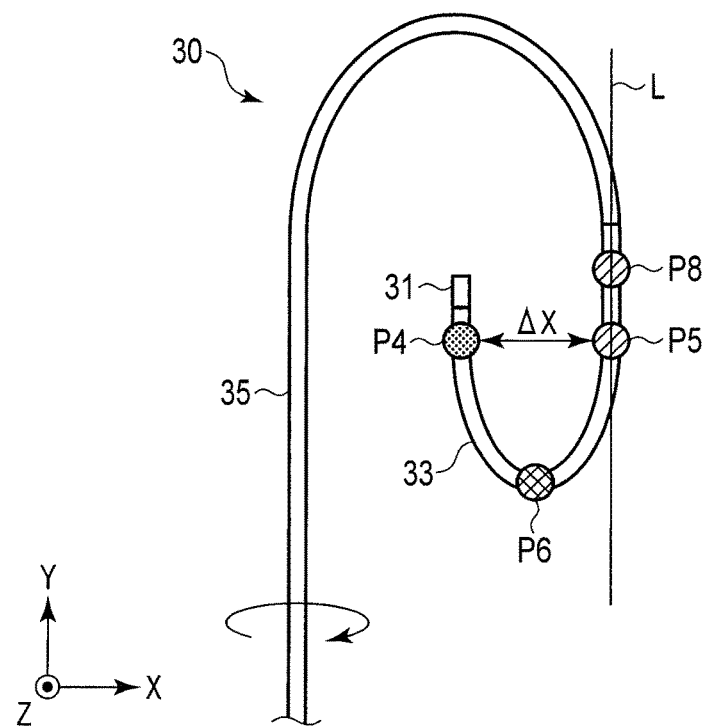
F I G. 13A
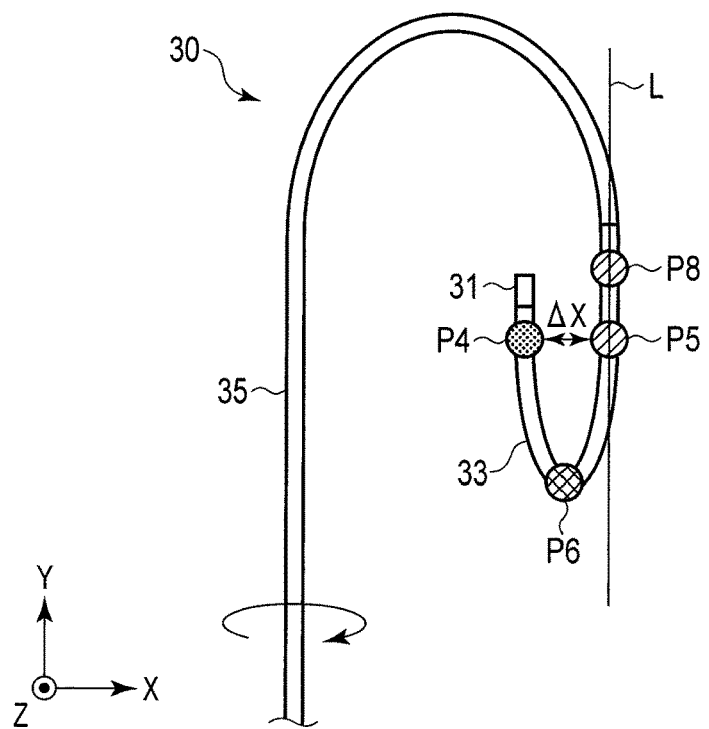
F I G. 13B

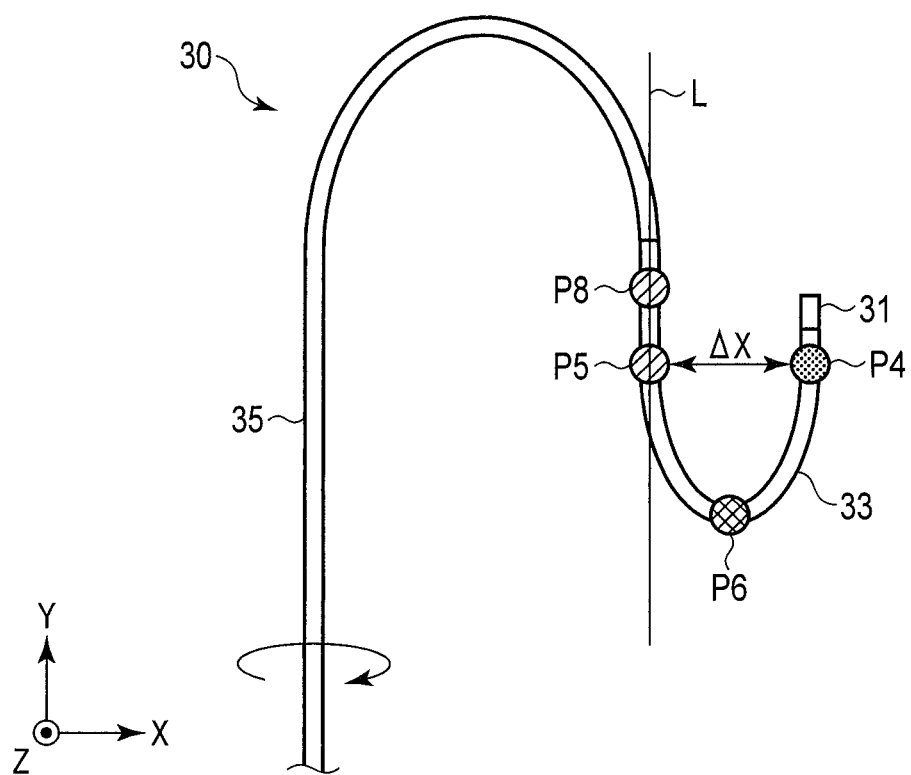
F I G. 13C

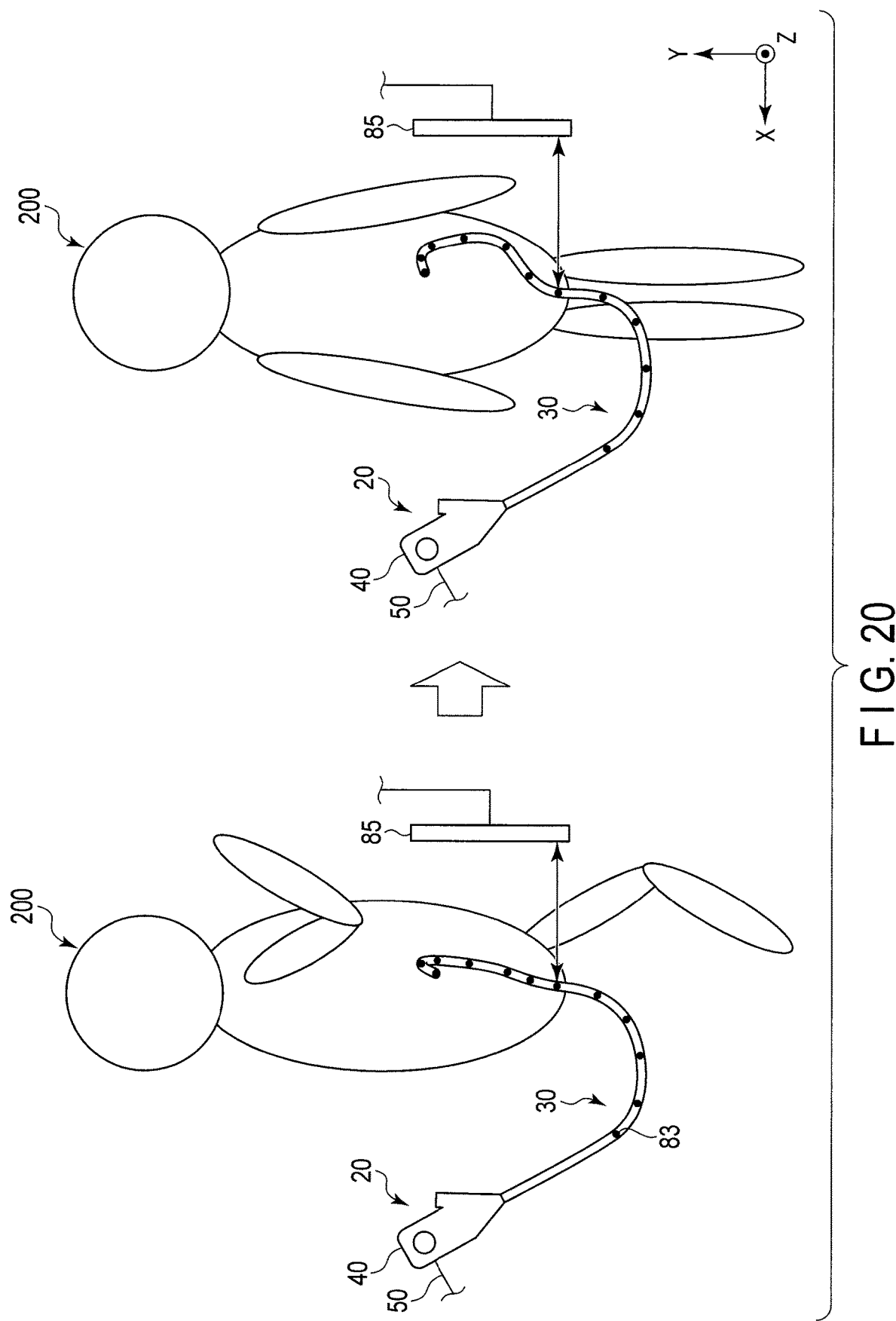
F I G. 20

INSERTION SUPPORT SYSTEM AND INSERTION SUPPORT METHOD

CROSS-REFERENCE TO RELATED APPLICATIONS

This application is a Continuation Application of PCT Application No. PCT/JP2017/021625, filed Jun. 12, 2017, the entire contents of which are incorporated herein by reference.

BACKGROUND OF THE INVENTION

1. Field of the Invention

The present invention relates to an insertion support system and an insertion support method.

2. Description of the Related Art

For example, Jpn. Pat. Appln. KOKAI Publication No. 2000-175861 discloses an endoscope shape detection apparatus configured to detect a shape of an insertion section by magnetic shape detection processing with the use of a coil, further to detect a specific shape such as a loop of the insertion section, and to generate a warning according to the detection result. A specific shape such as a loop is detected as support information for inserting the insertion section.

BRIEF SUMMARY OF THE INVENTION

An insertion support system according to an aspect of the present invention includes a state acquisition apparatus configured to acquire first information. The first information includes at least one of: a plurality of pieces of position information related to a plurality of positions of an insertion section to be inserted into an insertion target body; and a plurality of pieces of direction vector information in a longitudinal axis direction of the insertion section. The insertion support system also includes a support information calculator configured to calculate second information related to a rotation quantity of the insertion section based on the first information, and an output section configured to output the second information.

An insertion support method according to another aspect of the present invention includes acquiring first information. The first information includes at least one of: a plurality of pieces of position information related to a plurality of positions of an insertion section to be inserted into an insertion target body; and a plurality of pieces of direction vector information in a longitudinal axis direction of the insertion section. The insertion support method also includes calculating second information related to a rotation quantity of the insertion section based on the first information, and outputting the second information.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram of an insertion support system according to a first embodiment of the present invention.

FIG. 4A is a diagram schematically showing a loop of an insertion section arranged on an X-Y plane.

FIG. 4B is a diagram schematically showing a loop of the insertion section arranged on a Y-Z plane.

FIG. 11A is a diagram showing a position relationship between a first rotation detection point and a first rotation reference point of the insertion section.

FIG. 11B is a diagram showing a position relationship between the first rotation detection point and the first rotation reference point of the insertion section in a process of changing into an N-shape.

FIG. 13A is a diagram showing a position relationship between the first rotation detection point and first and second rotation reference points of the insertion section.

FIG. 13B is a diagram showing a position relationship between the first rotation detection point and the first and second rotation reference points of the insertion section in the process of changing into an N shape.

FIG. 13C is a diagram showing a position relationship between the first rotation detection point and the first and second rotation reference points of the N-shaped insertion section.

FIG. 20 is a diagram illustrating improvement of accuracy in determination of whether rotation of the insertion section is caused by a rotation operation instead of a postural change, or by a postural change.

DETAILED DESCRIPTION OF THE INVENTION

Figure 2:
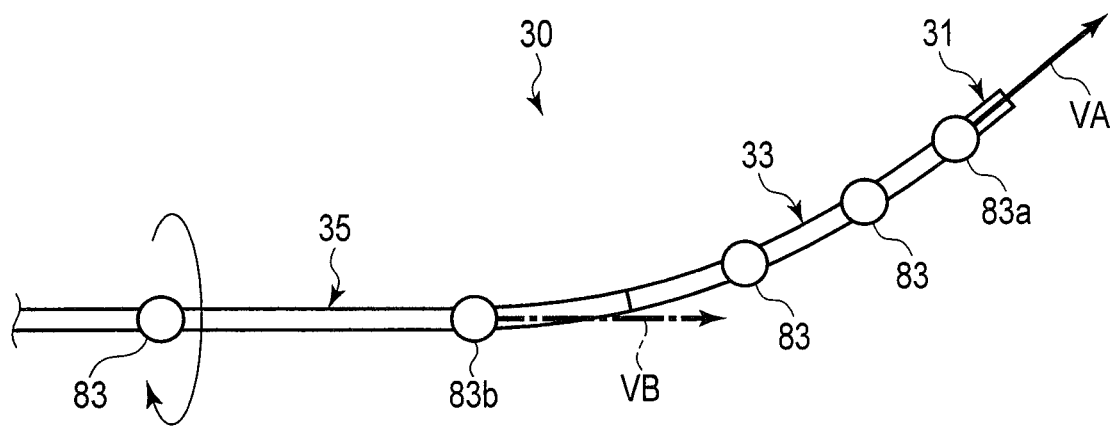
FIG. 2 is a diagram schematically showing an arrangement of a magnetic field generator at a bendable section and a distal end of a flexible tube section.

Hereinafter, embodiments of the present invention will be described in detail with reference to the accompanying drawings. In some of the drawings, illustrations of some members are omitted to achieve clarified illustrations.

First Embodiment

A first embodiment will be described with reference to FIGS. 1 to 5.

As shown in FIG. 1, an insertion support system 10 includes an insertion apparatus 20, a control device 60, a display 70, and a magnetic state acquisition apparatus 80.

The insertion apparatus 20 of the present embodiment is described, for example, as, but not limited to, a flexible large intestine endoscope for medical use. It suffices that the insertion apparatus 20 includes a flexible insertion section 30 to be inserted into an insertion target body, such as a flexible endoscope for medical use, a flexible endoscope for industrial use, a catheter, or a treatment instrument. The insertion target body is not limited to a human and may be, for example, an animal or other structure. The insertion apparatus 20 may be an observation apparatus that illuminates a target object of the insertion target body with illumination light and captures an image of the target object. The target object is, for example, an affected area or an area of lesion.

The insertion apparatus 20 includes the insertion section 30 to be inserted into an insertion target body, a control section 40 connected to a proximal end of the insertion section 30 and configured to operate the insertion apparatus 20, and a cord 50 connected to the control section 40. The cord 50 includes a connector (not shown) that is arranged at an end of the cord 50 and is attachable to and detachable from the control device 60.

The insertion section 30 is, for example, hollow and elongated. The insertion section 30 includes, in order of position from its distal end to its proximal end, a distal end hard section 31 in which various internal members (not shown) corresponding to the use of the insertion apparatus 20 are provided, a bendable section 33 that can be bent by a desired quantity in a desired direction, and a flexible tube section 35 that is flexible and is bent by an external force. The distal end hard section 31 and the bendable section 33 are shorter than the flexible tube section 35. Therefore, in the present embodiment, the distal end hard section 31, the bendable section 33, and the distal end of the flexible tube section 35 are regarded as the distal end of the insertion section 30.

The distal end hard section 31 includes an imaging element (not shown) configured to image the inside of an insertion target body or a target object. The imaging element includes a CCD or a CMOS. The imaging element is electrically connected to an electric signal line (not shown) provided inside the insertion section 30, the control section 40, and the cord 50. When the connector is connected to the control device 60, the electric signal line is electrically connected to the control device 60. An image captured by the imaging element is transmitted as an electric signal to an image processor (not shown) provided in the control device 60 through the electric signal line. The image processor performs image processing on the image and outputs the processed image to the display 70, so that the display 70 displays the image. The distal end hard section 31 emits illumination light.

The bendable section 33 has a length of approximately 15 cm, for example. The bendable section 33 is connected to a bend control section (not shown) provided in the control section 40 through an operation wire (not shown) provided inside the insertion section 30. The bendable section 33 can be bent by a desired quantity in a desired direction by pulling the operation wire through the operation of the bend control section.

The control section 40 is held by one hand of the operator of the insertion support system 10. The operator inserts the insertion section 30 into the insertion target body from an opening of the insertion target body (such as the anus of a patient). The display 70 displays an image of the inside of the insertion target body captured by the imaging element. Then, the operator observes and treats the inside of the insertion target body while viewing the image displayed on the display 70.

The control device 60 includes an image processor (not shown), a support information calculator 61, an output section 63, a detection controller 81, and a position shape acquisition section 87. At least one of the image processor, the support information calculator 61, the output section 63, the detection controller 81, and the position shape acquisition section 87 is configured by a hardware circuit including, for example, an ASIC. At least one of these elements may be configured by a processor. When at least one of these elements is configured by a processor, an internal memory or an external memory (not shown) configured to be accessed by the processor is provided in the control device 60. The internal memory or the external memory stores a program code for causing the processor to function as at least one of these elements when executed by the processor. Also, the image processor, the support information calculator 61, the output section 63, the detection controller 81, and the position shape acquisition section 87 may be configured by using either one or a plurality of processors. In the latter case, the processors can cooperate by transmitting and receiving data to and from each other. Also, in the latter case, the processors can be arranged in different housings.

The display 70 is a common display device, such as a liquid crystal display, a CRT display, or an organic EL display. The display 70 displays an image captured by the imaging element. As will be described in detail later, the display 70 displays second information relating to the rotation quantity of the insertion section 30, which is support information for inserting the insertion section 30.

The state acquisition apparatus 80 includes a detection controller 81, a plurality of magnetic field generators 83, a magnetic field detector 85, and a position shape acquisition section 87.

The detection controller 81 is electrically connected to the magnetic field generators 83 through an electric signal line 89. For clarity of illustration, only one electric signal line 89 is shown across the respective magnetic field generators 83; however, in reality, two electric signal lines 89 are connected to each magnetic field generator 83, and each electric signal line 89 is connected to the detection controller 81.

The detection controller 81 outputs an electric signal for generating a magnetic field to each of the magnetic field generators 83. This electric signal is, for example, a current of a sine wave. The detection controller 81 controls the magnetic field generator 83 using this current. The electric signal is output to each of the magnetic field generators 83 in a predetermined order. The determined order indicates, for example, the order of position from the magnetic field generator 83, provided on the distal side of the insertion section 30, toward the magnetic field generator 83, provided on the proximal side of the insertion section 30. The detection controller 81 may either always output a signal when the insertion support system 10 is driven, or output a signal merely at a desired timing.

Each of the magnetic field generators 83 receives an electric signal and generates a magnetic field. Each of the magnetic field generators 83 is disposed, for example, inside the insertion section 30. The magnetic field generators 83 are arranged at different positions in the longitudinal axis direction of the insertion section 30, for example, at equal distances apart with respect to each other. The magnetic field generators 83 are arranged in a line along the entire length of the insertion section 30. In the present embodiment, for example, three magnetic field generators 83 are arranged in the bendable section 33, and one magnetic field generator 83 is arranged at least at the distal end of the flexible tube section 35 connected to the bendable section 33. For example, the three magnetic field generators 83 arranged in the bendable section 33 are arranged at the distal end of the bendable section 33, the proximal end of the bendable section 33, and the middle of the distal end and the proximal end of the bendable section 33, respectively. The magnetic field generators 83 are configured by, for example, a magnetic coil.

The magnetic field detector 85 is arranged near an insertion target body. For example, the magnetic field detector 85 is arranged on the ceiling of a room where the insertion support system 10 is used, or on a bed upon which a patient as an insertion target body lies, and fixed in place. For example, the magnetic field detector 85 is an antenna, and the antenna is formed of a plurality of coils. The coils differ from each other in at least one of position and orientation. The magnetic field detector 85 detects the intensity of a plurality of magnetic fields generated from the respective magnetic field generators 83 and outputs the detected intensity to the position shape acquisition section 87 as an electric signal. The intensity of the magnetic field changes according to the distance between the magnetic field generator 83 and the magnetic field detector 85, or the orientation of the magnetic field generator 83 with respect to the magnetic field detector 85.

The coil generates a magnetic field and the antenna detects the magnetic field; however, the present embodiment need not be limited thereto. One of the coil and the antenna may generate a magnetic field, and the other of the coil and the antenna may detect the magnetic field. Therefore, one of the magnetic field generator 83 and the magnetic field detector 85 may be arranged in the insertion section 30, and the other may be arranged outside the insertion section 30 and fixed in place.

Based on the intensity of a plurality of magnetic fields detected by the magnetic field detector 85, the position shape acquisition section 87 acquires a plurality of pieces of position information related to the positions of the magnetic field generators 83 and a plurality of pieces of direction vector information related to the direction vectors of the magnetic field generators 83. For example, the position information indicates position coordinates, and the direction vector indicates a vector related to the longitudinal axis direction of the insertion section 30. Based on the plurality of pieces of position information and the plurality of pieces of direction vector information, the position shape acquisition section 87 acquires a plurality of pieces of position information of the insertion section 30, related to the position of the insertion section 30, and a plurality of pieces of direction vector information of the insertion section 30, related to the direction vector of the insertion section 30. The plurality of pieces of position information of the insertion section 30 indicate a plurality of position coordinates of the insertion section 30.

As described above, the state acquisition apparatus 80 calculates the plurality of pieces of position information and the plurality of pieces of direction vector information. The state acquisition apparatus 80 is only required to acquire first information that is needed at least according to a method of calculating a rotation quantity described later and included in the plurality of pieces of position information of the insertion section 30 and the plurality of pieces of direction vector information of the insertion section 30.

The position shape acquisition section 87 further acquires shape information of the insertion section 30 based on the plurality of pieces of position information of the insertion section 30. The position shape acquisition section 87 outputs the acquired first information and shape information of the insertion section 30 to the support information calculator 61. The position shape acquisition section 87 may output at least one of the first information and the shape information of the insertion section 30 acquired to the display 70 through the output section 63.

The position shape acquisition section 87 may acquire the plurality of pieces of position information of the insertion section 30 by interpolating the position information of each magnetic field generator 83 using spline processing or the like as necessary.

The position shape acquisition section 87 may always acquire the information when the insertion support system 10 is driven, acquire the information at a desired timing, or acquire the information when a detection result is input from the magnetic field detector 85.

The coil of the magnetic field generator 83 is a single-axis coil, and the central axis of the coil is along the longitudinal axis of the insertion section 30. When the insertion section 30 is bent and the orientation of the insertion section 30 is changed, the direction of the axis of one coil arranged in the bent part is changed, and the intensity of the magnetic field detected by the magnetic field detector 85 is changed. Therefore, the position shape acquisition section 87 can acquire the direction of the coil, that is, the direction vector information based on the intensity of the magnetic field changed in the one coil.

However, the situation is different when a rotation operation is performed. First, the rotation operation performed in the present embodiment will be described. For example, the proximal side of the insertion section 30 is twisted about the central axis of the insertion section 30 (for example, clockwise) with one hand of an operator, while the proximal side of the insertion section 30 is gripped by one hand of the operator. The twisting force of the operator applied from one hand to the proximal side of the insertion section 30 is transmitted from the proximal side of the insertion section 30 to the distal side of the insertion section 30. Thereby, the insertion section 30 is twisted clockwise about the central axis of the insertion section 30. Therefore, the rotation operation indicates an operation of twisting the insertion section 30, and the rotation quantity is a twist quantity about the longitudinal axis of the insertion section 30.

When the operator performs a rotation operation on the insertion section 30 in an about linear state, the orientation of the insertion section 30 does not change as compared to the orientation thereof before the rotation operation. Thus, regardless of where in the insertion section 30 the coil being the magnetic field generator 83 is arranged, the coil rotates about its axis, and the intensity of the magnetic field detected by the magnetic field detector 85 does not change as compared to the intensity of the magnetic field before the rotation operation. As such, when the insertion section 30 is in an about linear state, the position shape acquisition section 87 cannot acquire the rotation quantity of the coil being the magnetic field generator 83, that is, the rotation quantity of the insertion section 30 based on the intensity of the magnetic field.

It is assumed that two coils are arranged at the same position in the insertion section 30, and that the directions of the axes of the coils are different. In this case, when the rotation operation is performed, the direction of the axis of one of the two coils changes, and the intensity of the magnetic field changes. Therefore, the position shape acquisition section 87 can acquire the rotation quantity of the coils, that is, the rotation quantity of the insertion section 30 based on the changed intensity of the magnetic field. However, the internal space of the elongated member such as the insertion section 30 is narrow, and it is not easy to arrange two coils. Also, when two coils are arranged, the insertion section 30 becomes thick, likely causing decrease of the insertability of the insertion section 30.

Accordingly, the support information calculator 61 calculates the second information related to the rotation quantity of the insertion section 30, which serves as support information for inserting the insertion section 30, based on the first information acquired by the position shape acquisition section 87. In the present embodiment, the plurality of pieces of direction vector information is adopted as the first information. The support information calculator 61 may always perform calculation when the insertion support system 10 is driven, perform calculation at a desired timing, or perform calculation when an acquisition result is input from the position shape acquisition section 87.

The premise for the calculation will be described first; a description of the calculation by the support information calculator 61 then follows.

FIG. 2 shows the insertion section 30 and the magnetic field generator 83, which is a single-axis coil disposed inside the insertion section 30. As described above, even if the rotation operation is performed on the insertion section 30 in an about linear state, and the magnetic field generator 83 as a coil rotates about its axis, the position shape acquisition section 87 cannot detect the rotation quantity of the insertion section 30. In the present embodiment, since the support information calculator 61 calculates the rotation quantity of the insertion section 30, two magnetic field generators 83 at two locations are used. The two magnetic field generators 83 are, for example, a magnetic field generator 83a arranged at the first position from the distal end of the insertion section 30, and a magnetic field generator 83b arranged on the distal side of the insertion section 30 excluding the bendable section 33, that is, arranged at the fourth position from the distal end of the insertion section 30. In the present embodiment, the direction vector information of the magnetic field generator 83a is a rotation detection vector VA, and the direction vector information of the magnetic field generator 83b is a reference vector VB. The rotation detection vector VA is a vector for detecting the rotation quantity of the insertion section 30. The reference vector VB serves as a reference for the rotation detection vector VA.

Although not shown in the figures, even if the two magnetic field generators 83a and 83b are used, if the rotation detection vector VA and the reference vector VB are oriented in the same direction, the support information calculator 61 cannot calculate the rotation quantity of the insertion section 30. Therefore, in order to calculate the rotation quantity of the insertion section 30 using the two magnetic field generators 83a and 83b, the bendable section 33 needs to be bent in advance with respect to the distal end of the flexible tube section 35. Therefore, when the support information calculator 61 calculates the rotation quantity of the insertion section 30, the support information calculator 61 outputs an instruction to the display 70 through the output section 63. For example, when the display 70 receives this instruction, the display 70 displays to the operator a message indicating that the bendable section 33 needs to be bent. When the operator who has acknowledged the message bends the bendable section 33 through the bend control section, the shape information of the insertion section 30 acquired by the position shape acquisition section 87 is input to the support information calculator 61, and the support information calculator 61 determines that the bendable section 33 is bent based on the shape information of the insertion section 30. The support information calculator 61 can calculate the rotation quantity of the insertion section 30. As a result, even if the flexible tube section 35 is in an about linear state, the rotation quantity of the insertion section 30 is calculated because the bendable section 33 is bent with respect to the distal end of the flexible tube section 35 by the bending operation performed by the operator, and the magnetic field generators 83a and 83b used to detect the rotation quantity face in different directions.

The display 70 need not necessarily display the message. Depending on the usage of the rotation quantity, the support information calculator 61 may determine whether or not the bendable section 33 is bent based on the shape information of the insertion section 30. The support information calculator 61 may calculate the rotation quantity of the insertion section 30 only when the support information calculator 61 determines that the bending is performed. When the support information calculator 61 determines that the bending is not performed, the support information calculator 61 may output an instruction to the display 70 through the output section 63, as described above.

Let us assume that when the support information calculator 61 calculates the rotation quantity of the insertion section 30, the relative direction of the rotation detection vector VA and the reference vector VB has changed due to factors other than the rotation operation. In this case, a calculation error of the rotation quantity of the insertion section 30 is caused. Therefore, while the rotation operation is being performed, the display 70 may display a message that the bending operation on the bendable section 33 is suspended so that the bendable section 33 is not bent. Thereby, the calculation accuracy is improved.

Next, an example of the calculation of the rotation quantity of the insertion section 30 by the support information calculator 61 will be concretely described.

Although not shown in the figures, when the insertion section 30 has already been inserted into an insertion target body and has a certain shape such as an about linear shape, and an insertion operation (such as a rotation operation) is performed on the insertion section 30, the shape of the insertion section 30 may change to another shape depending on the shape of the insertion target body and the insertion operation, causing the orientation of the distal end of the insertion section 30 to change inside the insertion target body. That is, although not shown in the figures, the direction of the reference vector VB as a reference changes as compared to that before the insertion operation including the rotation operation is performed, causing both the direction of the rotation detection vector VA and the direction of the reference vector VB to change. In other words, when the shape of the insertion section 30 changes, the rotation detection vector VA includes factors other than the rotation operation, and the direction of the rotation detection vector VA changes. Thus, the direction of the rotation detection vector VA changes due to factors other than the rotation operation, and in this state the support information calculator 61 cannot calculate the rotation quantity of the insertion section 30 based on the rotation detection vector VA. Another shape mentioned above is, for example, a loop shape. The loop in the present application is not limited to a circular state, and includes a state in which a part of the insertion section 30 has an arc shape.

Therefore, the support information calculator 61 performs a rotation calculation for obtaining the rotation vector VA in a state where the reference vector VB is oriented in the same direction before and after the insertion operation. In this context, the X-axis, the Y-axis orthogonal to the X-axis, and the Z-axis orthogonal to the X-axis and the Y-axis are defined. The reference vector VB is oriented in the Y-axis direction before the insertion operation including the rotation operation is performed. The shape of the insertion section 30 is changed after the insertion operation including the rotation operation is performed, and the reference vector VB is oriented in a direction different from the Y-axis due to the change. In order to obtain the rotation detection vector VA in a state where the reference vector VB is oriented in the Y-axis direction, the support information calculator 61 performs a rotation calculation on the rotation detection vector VA. As a result, the support information calculator 61 can calculate the rotation quantity of the insertion section 30 based on the rotation detection vector VA.

Figure 3:
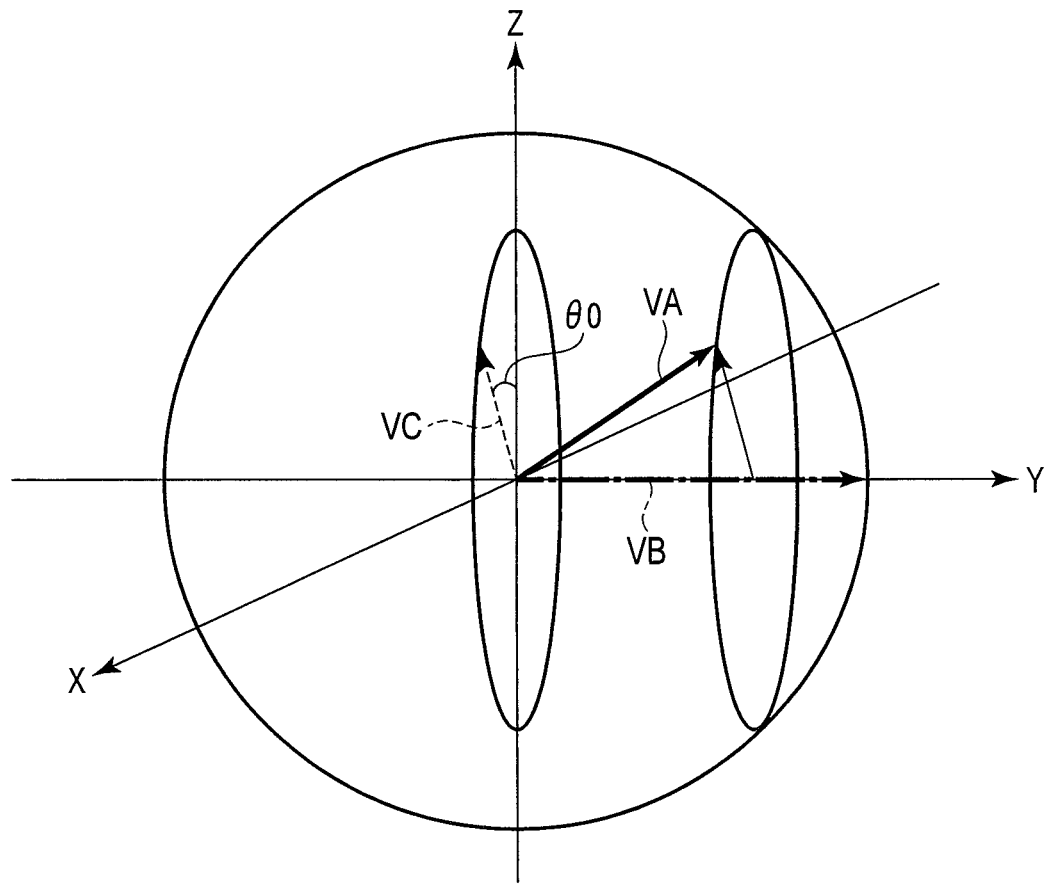
FIG. 3 is a diagram showing a relationship of a projection vector with a rotation detection vector and a reference vector.

An example of the rotation calculation for obtaining the rotation detection vector VA so that the reference vector VB ($Vx_0$, $Vy_0$, $Vz_0$) is oriented in the Y-axis direction will be described. First, the support information calculator 61 calculates a rotation matrix for rotation about the Z-axis in which the X-axis component of the rotation detection vector VA is 0 (0, $Vy_1$, $Vz_1$). Thereafter, the support information calculator 61 calculates a rotation matrix for rotation about the X-axis in which the Z-axis component is 0 (0, $Vy_2$, 0). Next, the support information calculator 61 performs the same rotation calculation on the rotation detection vector VA using the calculated rotation matrix about the Z-axis and the X-axis. Thereby, the rotation detection vector VA in a state where the reference vector VB is oriented in the Y-axis direction is obtained. That is, the rotation detection vector VA after the rotation operation in a state where the directional change due to factors other than the rotation operation has been eliminated or reduced is obtained with respect to the rotation detection vector VA before the insertion operation. FIG. 3 shows the rotation detection vector VA and the reference vector VB after the rotation calculation. Next, the support information calculator 61 calculates an angle θ0 between a vector obtained by projecting the rotation detection vector VA on the X-Z plane (hereinafter referred to as a "projection vector VC") and the Z-axis as the rotation quantity of the insertion section 30 with respect to the Z-axis.

That is, the support information calculator 61 performs a rotation calculation that causes the reference vector VB after the rotation operation of the insertion section 30 to be oriented in the same direction as the reference vector VB before the rotation operation of the insertion section 30, on the rotation detection vector VA after the rotation operation. Also, the support information calculator 61 calculates the rotation quantity of the insertion section 30 based on the rotation detection vector VA rotated by the rotation calculation performed on the rotation detection vector after the rotation operation. The expression "before the rotation operation of the insertion section 30" in this context indicates a state (e.g., an about linear shape) before the shape of the insertion section 30 is deformed by the insertion operation. Also, the expression "after the rotation operation of the insertion section 30" indicates a state (e.g., a loop shape) after the shape of the insertion section 30 is deformed by the insertion operation. Therefore, the support information calculator 61 calculates the rotation quantity of the insertion section 30 based on the changes in a plurality of pieces of direction vector information such as the rotation detection vector VA and the reference vector VB.

Let us assume that while the support information calculator 61 is calculating the rotation quantity of the insertion section 30, the relative direction of the rotation detection vector VA and the reference vector VB has changed due to factors other than the rotation operation, as described above. In this case, a calculation error of the rotation quantity of the insertion section 30 occurs. However, as an exception, a directional change of the rotation detection vector VA that does not cause the direction of the projection vector VC to change but causes only the magnitude of the projection vector VC to change, does not lead to a calculation error.

It is even more preferable that the rotation calculation that causes the reference vector VB to be oriented in the Y-axis direction be changed according to the shape of the insertion section 30. Usually, in a supine position where a patient as an insertion target body lies on the patient's back, for example, the loop of the insertion section 30 scarcely spreads in the direction of the patient's abdomen and back, due to the structure of the large intestine of the patient as an insertion target body, and tends to spread in the direction from one flank toward the other flank of the patient and in the direction from the anus to the diaphragm of the patient. In FIGS. 4A and 4B, the Y-axis direction indicates the direction from the anus toward the diaphragm, and the Z-axis direction indicates the direction from the back toward the abdomen.

In general, when the patient is in a supine position, for example, the loop of the insertion section 30 is often formed on a plane parallel to the X-Y plane and spreads on the plane parallel to the X-Y plane, as shown in FIG. 4A. Therefore, when the rotation operation is performed in the order of rotation about the Z-axis and rotation about the X-axis, the loop is eliminated and the insertion section 30 returns to an about linear shape.

It is also conceivable that a loop is formed on a plane parallel to the Y-Z plane, as shown in FIG. 4B. When the rotation calculation is performed on the insertion section 30 looped in this manner in the order of calculation of the rotation matrix for rotation about the Z-axis and calculation of the rotation matrix for rotation about the X-axis, as described above, factors other than the rotation operation cannot be removed. Therefore, the support information calculator 61 cannot calculate the rotation quantity of the insertion section 30 with respect to the Z-axis. Therefore, when a loop is formed on the Y-Z plane as shown in FIG. 4B, the rotation calculation is performed, for example, in the order of calculation of the rotation matrix for rotation about the X-axis and calculation of the rotation matrix for rotation about the Z-axis. Then, factors other than the rotation operation are removed. Also, the support information calculator 61 can calculate the rotation quantity of the insertion section 30 with respect to the Z-axis.

As described above, the support information calculator 61 can calculate the rotation quantity corresponding to various shapes of the insertion section 30 by changing the order of calculation of the rotation matrix according to the direction of the loop. In addition, the accuracy of the rotation calculation of the vector increases with the performance of a calculation to return the shape of the portion of the insertion section 30 on the control section 40 side with respect to the reference vector VB to the shape before the rotation operation.

Figure 5:
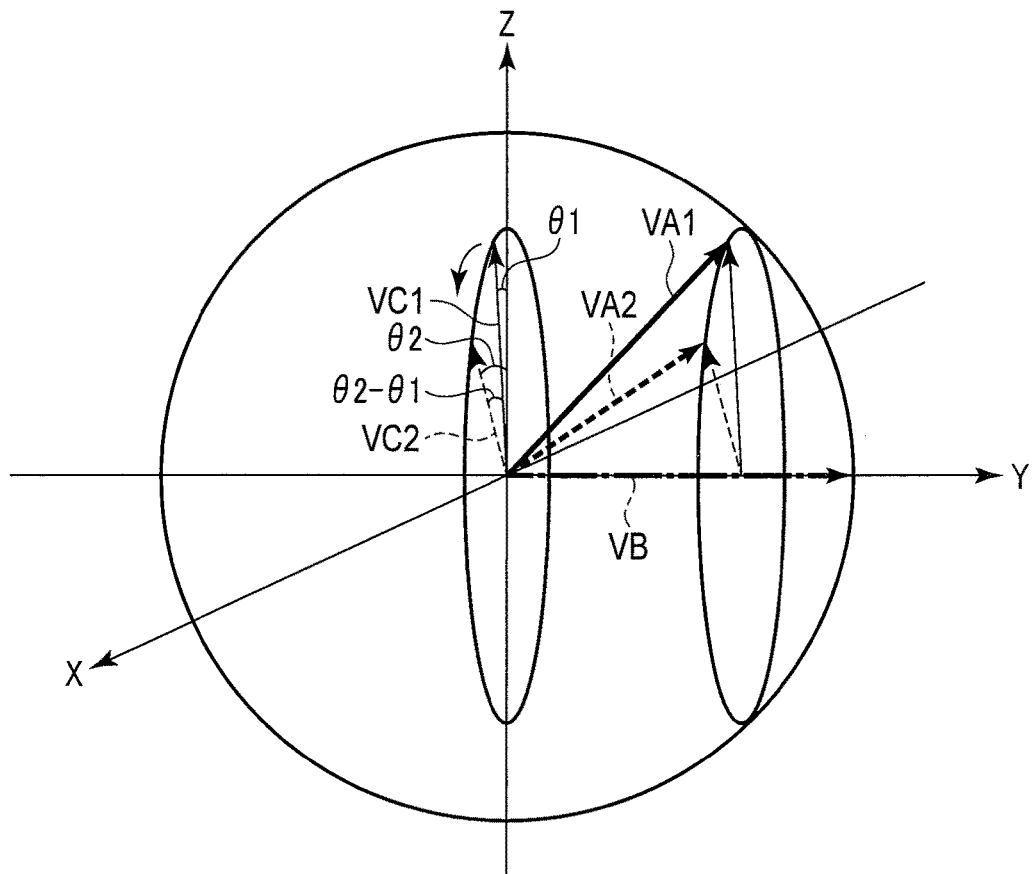
FIG. 5 is a diagram for illustrating calculation of a rotation quantity of the insertion section by a support information calculator based on any angle using the rotation detection vector.

The support information calculator 61 calculates the rotation quantity of the insertion section 30 with respect to the Z-axis; however, the support information calculator 61 is not limited thereto. The support information calculator 61 may calculate the rotation quantity of the insertion section 30 with respect to the X-axis or the Y-axis. Also, the support information calculator 61 may calculate the rotation quantity of the insertion section 30 based on any angle. As shown in FIG. 5, for example, a rotation detection vector at the time when a switch (not shown) arranged in the control section 40 is pressed is defined as "a rotation detection vector VA1", a projection vector of the rotation detection vector VA1 is defined as "a projection vector VC1", and an angle between the projection vector VC1 and the Z-axis is defined as "an angle θ1". Also, a rotation detection vector after the insertion section further rotates is defined as "a rotation detection vector VA2", a projection vector of the rotation detection vector VA2 is defined as "a projection vector VC2", and an angle between the projection vector VC2 and the Z-axis is defined as "an angle θ2". The support information calculator 61 calculates the angles θ1 and θ2 as the rotation quantity of the insertion section 30 with respect to the Z-axis. Then, the support information calculator 61 calculates an angle (θ2−θ1) as the rotation quantity of the insertion section 30 from the time when the switch is pressed.

The present embodiment has been described using the direction vector information (rotation detection vector VA) of the magnetic field generator 83a and the direction vector information (reference vector VB) of the magnetic field generator 83b; however, the present embodiment is not limited thereto. For example, direction vector information of another magnetic field generator 83 arranged in the insertion section 30 may be used.

The rotation quantity of the insertion section 30 calculated by the support information calculator 61 is transmitted to the output section 63. The output section 63 outputs the rotation quantity of the insertion section 30 to the outside of the control device 60, for example, to the display 70. The display 70 displays the rotation quantity of the insertion section 30 with a character and a symbol, for example. The display 70 may output the rotation quantity of the insertion section 30 by sound.

The output destination of the output section 63 is not limited to the display 70. For example, the output section 63 may feedback the rotation quantity of the insertion section 30 to a support system (not shown) configured to present support information supporting the insertion operation. The support system may present support information including the rotation quantity of the insertion section 30 to the operator. Information included in the support information is not limited to the rotation quantity of the insertion section 30 calculated by the support information calculator 61 based on the calculation result of the state acquisition apparatus 80. For example, a gravity sensor is disposed in the control section 40 or the insertion section 30 and calculates a directional change of the gravity. The support information may include the rotation quantity of the insertion section 30 calculated by the support information calculator 61 based on the calculation result of the gravity sensor. The rotation quantity of the bend control section may be detected by a rotary encoder or a potentiometer, and the rotation quantity of the bend control section may be presented as support information.

The control device 60 may include a storage section (not shown) configured to store the rotation quantity of the insertion section 30, and the output section 63 may output the rotation quantity of the insertion section 30 to the storage section as an output destination.

When the direction of the projection vector VC changes due to factors other than the rotation operation, a calculation error of the rotation quantity of the insertion section 30 occurs. Thus, an example of determining whether a directional change of the projection vector VC is caused by the rotation operation or caused by the bending of the bendable section 33 is shown.

When the bendable section 33 is bent, a change of the shape of the portions of the insertion section 30 other than the bendable section 33, that is, a change of the position coordinates of the insertion section 30 is usually small. On the other hand, when a rotation operation to return the loop shape to an about linear shape is performed, the change of the position coordinates of the portions of the insertion section 30 other than the bendable section 33 is large. Thus, a threshold is set in advance for the average of the changes of a plurality of position coordinates of the portions (e.g., the flexible tube section 35) other than the bendable section 33 before and after the directional change of the projection vector VC. When the average of the changes of the coordinates is less than the threshold, the change of the shape of the insertion section 30 is small. Therefore, the support information calculator 61 determines that the direction of the projection vector VC has changed due to the bending of the bendable section 33. As such, the support information calculator 61 does not calculate the rotation quantity of the insertion section 30, that is, sets the rotation quantity of the insertion section 30 to 0°. When the average of the changes of the coordinates is equal to or greater than the threshold, the change of the shape of the insertion section 30 is large. Therefore, the support information calculator 61 determines that the direction of the projection vector VC has changed due to the rotation operation. As such, the support information calculator 61 calculates the rotation quantity of the insertion section 30.

The plurality of pieces of direction vector information as the first information used in the present embodiment is based on the direction vector information of the magnetic field generator 83; however, a plurality of pieces of direction vector information detected by other methods may be used. For example, the direction vector information as the first information may be calculated based on the position information of the plurality of magnetic field generators 83, and/or by interpolating the position information of each of the magnetic field generators 83. For example, with respect to a point $P_i$ for calculating the direction vector, position information of a point $P_{i-1}$ adjacent to the distal side of the insertion section 30 and a point $P_{i+1}$ adjacent to the control section 40 side of the insertion section 30 in the longitudinal direction of the insertion section 30 may be used to set $P_{i-1}$–$P_{i+1}$ as the direction vector of P.

In the present embodiment, the support information calculator 61 calculates the rotation quantity of the insertion section 30 based on the plurality of pieces of direction vector information of the plurality of magnetic field generators 83. As a result, even if a magnetic state detection unit using a single-axis coil is arranged, the rotation quantity of the insertion section 30 can be calculated, and the rotation quantity can be output by the output section 63. For example, the output section 63 outputs the rotation quantity of the insertion section 30 to the display 70, and the display 70 displays the rotation quantity. As a result, the rotation quantity of the insertion section 30 that cannot be directly seen due to insertion thereof into the insertion target body can be provided to the operator as support information for insertion, allowing for support of the insertion and improvement of the insertability.

In the present embodiment, even if the direction of the rotation detection vector VA changes due to factors other than the rotation operation, the rotation detection vector VA in a state where the direction of the reference vector VB is oriented in the Y-axis direction is obtained by the rotation calculation. In other words, the direction of the rotation detection vector VA is returned by the rotation calculation. Put another way, the rotation detection vector VA after the rotation operation is obtained in a state where the directional change due to factors other than the rotation operation has been eliminated or reduced. Also, the support information calculator 61 can calculate the rotation quantity of the insertion section 30 based on the rotation detection vector VA. That is, even if the orientation of the distal end of the insertion section 30 changes before and after the insertion operation inside the insertion target body, the rotation quantity of the insertion section 30 can be calculated.

[Modification 1]

A modification 1 of the present embodiment will be described below. In the present modification, only the differences from the first embodiment will be described. In the present modification, description is given by adopting a plurality of pieces of position information, specifically, a plurality of position coordinates as the first information.

Figure 6:
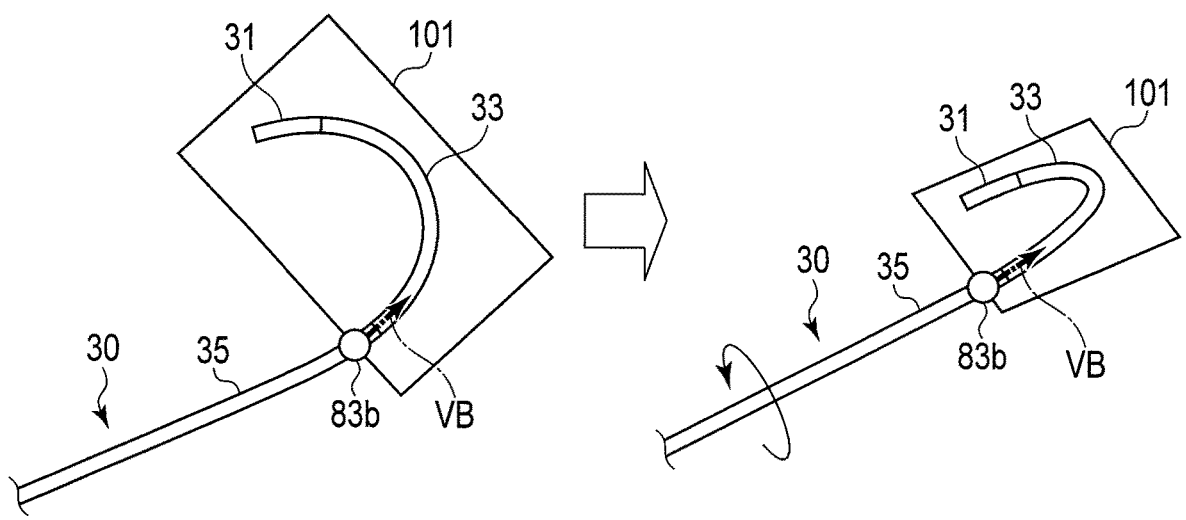
FIG. 6 is a diagram for illustrating a rotation detection plane that is rotated by rotation calculation.

As shown in FIG. 6, the support information calculator 61 according to the present modification calculates a plane (hereinafter referred to as a "rotation detection plane 101") on which the bendable section 33 is arranged, based on a plurality of pieces of position information (position coordinates) of the bendable section 33 acquired by the position shape acquisition section 87. The rotation detection plane 101 is a plane that approximates a plurality of pieces of position information (position coordinates), and is used to calculate the rotation quantity of the insertion section 30. The calculation of the rotation detection plane 101 can be performed by, for example, the commonly-known least-square method. In this modification, every position information (position coordinate) of the bendable section 33 is used as the plurality of pieces of position information (position coordinates) of the bendable section 33 in order to improve the calculation accuracy.

Hereinafter, an example of the calculation of the rotation quantity of the insertion section 30 by the support information calculator 61 in the present modification will be described.

First, attention is focused on the magnetic field generator 83*b* arranged on the distal side of the insertion section 30 excluding the bendable section 33. In the present modification, the direction vector information of the magnetic field generator 83*b* includes a reference vector VB. The reference vector VB serves as a reference for the rotation detection plane 101.

Figure 7:
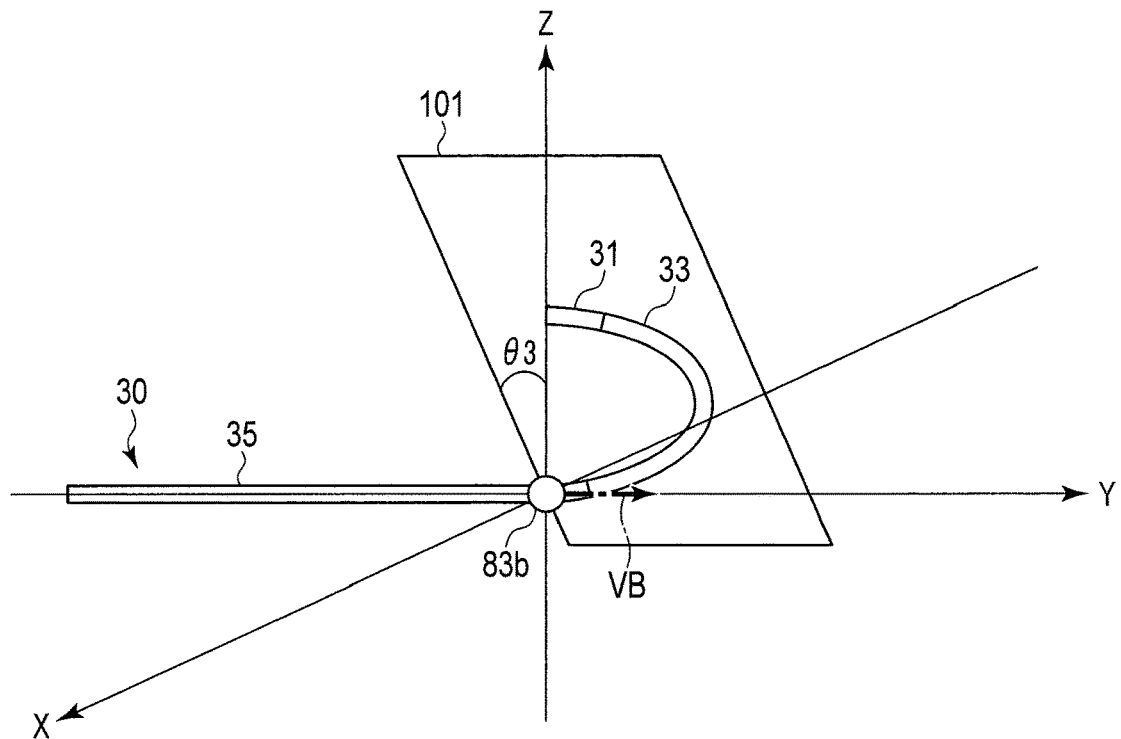
FIG. 7 is a diagram for illustrating calculation, by the support information calculator, of an angle between the reference Y-Z plane and the rotation detection plane as a rotation quantity of the insertion section.

In a manner similar to the first embodiment, a rotation calculation is performed on the rotation detection plane 101 in order to obtain a change of the angle of the rotation detection plane 101 in a state where the reference vector VB is oriented in the Y-axis direction. As a result, the support information calculator 61 can calculate the rotation quantity of the insertion section 30 based on the rotation detection plane 101. The rotation calculation performed on the rotation detection plane 101 is about the same as the rotation calculation performed on the rotation detection vector VA. FIG. 7 shows the rotation detection plane 101 after the rotation calculation and the reference vector VB. Next, the support information calculator 61 calculates an angle θ3 (see FIG. 7) between the Y-Z plane as a reference and the rotation detection plane 101 after rotation, as the rotation quantity of the insertion section 30 with respect to the Z-axis.

That is, the support information calculator 61 performs a rotation calculation that causes the reference vector VB after the rotation operation of the insertion section 30 to be oriented in the same direction as the reference vector VB before the rotation operation of the insertion section 30, on the rotation detection plane 101 after the rotation operation. Also, the support information calculator 61 calculates the rotation quantity of the insertion section 30, based on the change of the angle of the rotation detection plane 101 rotated by the rotation calculation that is performed on the rotation detection plane after the rotation operation. Therefore, the support information calculator 61 calculates the rotation detection plane 101 based on the first information, and calculates the rotation quantity of the insertion section 30 based on the change of the angle of the rotation detection plane 101 after rotation. In this example, the first information refers to a plurality of pieces of position information (position coordinates) of the bendable section 33. Also, the change of the angle of the rotation detection plane 101 indicates the rotation quantity of the rotation detection plane 101 rotated by the rotation operation.

Figure 8:
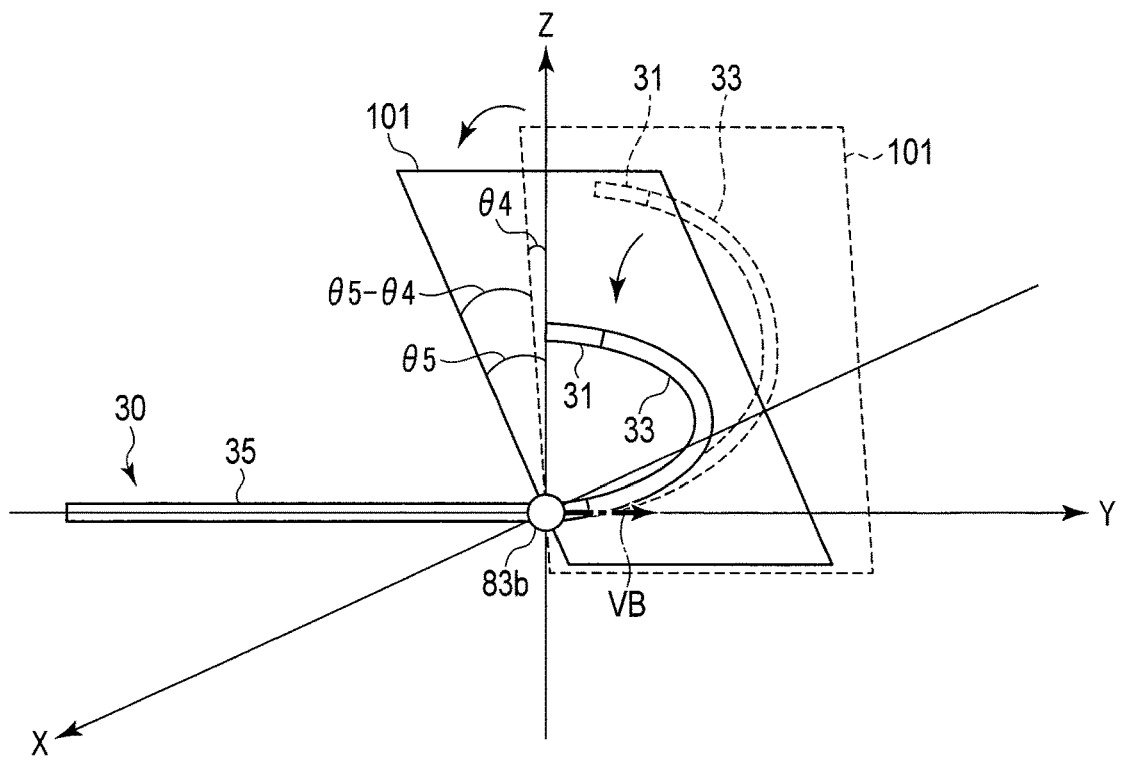
FIG. 8 is a diagram for illustrating calculation of a rotation quantity of the insertion section by the support information calculator based on any angle using the rotation detection plane.

The support information calculator 61 calculates the rotation quantity of the insertion section 30 with respect to the Z-axis; however, the support information calculator 61 is not limited thereto. The support information calculator 61 may calculate the rotation quantity of the insertion section 30 with respect to the X-axis or the Y-axis using the rotation detection plane 101. Also, the support information calculator 61 may calculate the rotation quantity of the insertion section 30 based on any angle using the rotation detection plane 101. As shown in FIG. 8, for example, an angle between the rotation detection plane 101 and the Y-Z plane at the time when a switch (not shown) arranged in the control section 40 is pressed is defined as "an angle θ4", and an angle between the rotation detection plane 101 after rotation as a result of further rotation of the insertion section and the Y-Z plane is defined as "an angle θ5". The support information calculator 61 calculates the angles θ4 and θ5 as the rotation quantity of the insertion section 30 with respect to the Y-Z plane. Then, the support information calculator 61 calculates an angle (θ5−θ4) as the rotation quantity of the insertion section 30 from the time at which the switch is pressed.

Figure 9:
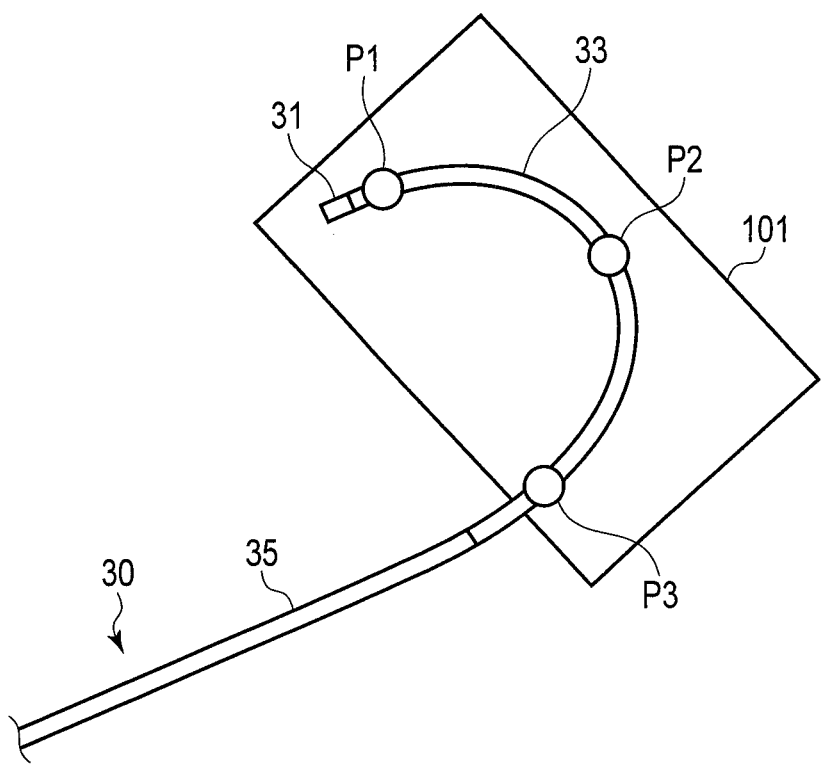
FIG. 9 is a diagram for illustrating calculation of the rotation detection plane by the support information calculator based on position information (position coordinates) at three points of the bendable section.

The plurality of pieces of position information (position coordinates) used to calculate the rotation detection plane 101 need not employ every position information (position coordinate) of the bendable section 33. For example, position information (position coordinates) of three points P1, P2, and P3 of the distal end, the proximal end, and the intermediate position between the distal end and the proximal end of the bendable section 33 may be used, as shown in FIG. 9. The support information calculator 61 calculates the rotation detection plane 101 on which they are arranged based on these pieces of position information (position coordinates). By reducing the position information (position coordinates) to be used, the amount of calculation is reduced, and the load on the support information calculator 61 is reduced.

Figure 10:
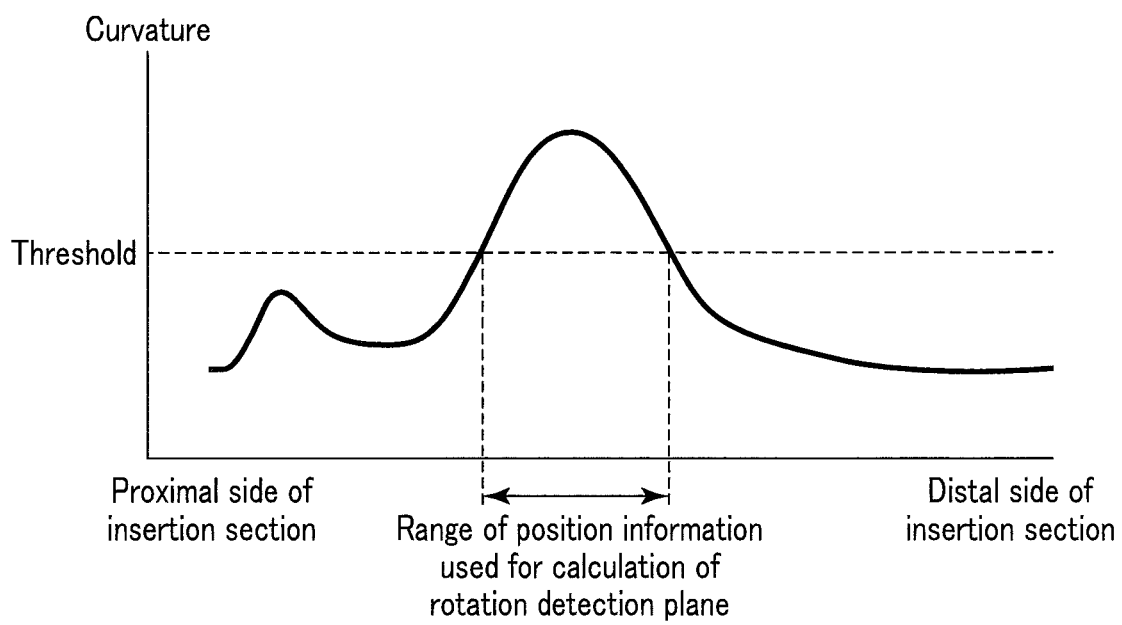
FIG. 10 is a diagram for illustrating calculation, by the support information calculator, of the rotation detection plane of a bent portion of the insertion section that has a curvature equal to or greater than a certain value.

As shown in FIG. 10, the position information (position coordinates) as the first information used to calculate the rotation detection plane 101 is not limited to the position information (position coordinates) of the bendable section 33, and may be a plurality of pieces of position information (position coordinates) of the curved portion of the insertion section 30 having a curvature equal to or greater than a certain value. Specifically, the support information calculator 61 calculates a curvature of the insertion section 30 based on the shape information of the insertion section 30. A threshold is set in advance for the curvature. Then, the support information calculator 61 calculates the rotation detection plane 101 using a plurality of pieces of position information (position coordinates) of the curved portion having a curvature equal to or greater than the threshold.

When the insertion section 30 is close to a straight line, the error of the rotation detection plane 101 may increase. When the insertion section 30 is completely linear, the rotation detection plane 101 is not fixed, and thus is not calculated. On the other hand, when the curvature of the insertion section 30 is calculated and the rotation detection plane 101 is calculated using position coordinates in a range where the curvature is equal to or greater than a certain value, the error of the rotation detection plane 101 is reduced. That is, the calculation error is also reduced.

[Modification 2]

A modification 2 of the present embodiment will be described below. In the present modification, only the differences from the first embodiment will be described. In the present modification, description is provided by adopting a plurality of pieces of position information, specifically, a plurality of position coordinates as the first information.

As shown in FIG. 11A, the insertion section 30 may loop due to the insertion operation of the insertion section 30 into the large intestine (not shown). Even if the insertion section 30 is pushed in this state, the loop merely expands and the insertion section 30 is not smoothly inserted. Also, the insertion section 30 may push the intestinal wall by expansion of the loop, causing the large intestine to extend and causing pain to the patient. Therefore, the insertion section 30 needs to be changed into an about linear shape together with the large intestine by an insertion manipulation.

Figure 11C:
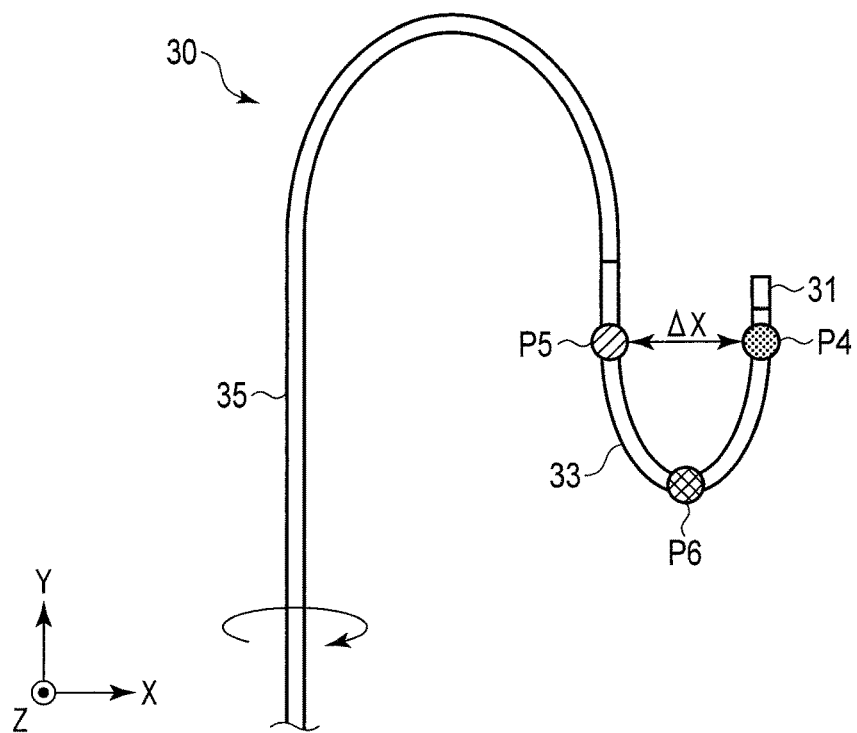
FIG. 11C is a diagram showing a position relationship between the first rotation detection point and the first rotation reference point of the N-shaped insertion section.

In a part of the process of changing from the loop shape to the about linear shape by the insertion manipulation, the insertion section 30 needs to be changed from the shape shown in FIG. 11A to the N-shape shown in FIG. 11C. For this change to take place, a clockwise rotation operation, for example, is performed. If the operator is able to know the extent to which the rotation operation should be performed during the rotation operation, the insertion is supported. That is, the rotation quantity of the insertion section 30 lacked by the insertion section 30 to change from the shape shown in FIG. 11A to an N-shape is needed as support information. Hereinafter, the rotation quantity is referred to as a "lacked rotation quantity".

Hereinafter, examples 1, 2, and 3 of the calculation of the lacked rotation quantity by the support information calculator 61 in the present modification will be described.

First, the example 1 will be described. The insertion section 30 is arranged on the X-Y plane. The distal end of the insertion section 30 is defined as "a rotation detection point P4 for detecting rotation". A point serving as a reference for rotation is referred to as "a first rotation reference point P5". The first rotation reference point P5 is set as the first point close to a value of the rotation detection point P4 on the Y-coordinate beyond a minimum point P6 on the Y-coordinate when viewed along the insertion section 30 from the distal end to the proximal side of the insertion section 30. There may be a plurality of minimums depending on the shape of the insertion section 30. When a plurality of minimum points exists, a minimum on the distal side of the insertion section 30 is defined as "the minimum point P6". The degree of proximity to the value of the rotation detection point P4 on the Y-coordinate may be set as desired. The first rotation reference point P5 is on the opposite side of the rotation detection point P4 in the X-axis direction with respect to the minimum point P6. The rotation detection point P4, the first rotation reference point P5, and the minimum point P6 may be set by the support information calculator 61 based on the shape information of the insertion section 30 acquired by the position shape acquisition section 87.

As shown in FIGS. 11A, 11B, and 11C, when the insertion section 30 rotates clockwise, the rotation detection point P4 moves from the left side of the first rotation reference point P5 to the right side of the first rotation reference point P5 so as to relatively turns about the first rotation reference point P5. When the insertion section 30 changes to an N-shape as shown in FIG. 11C, the position of the rotation detection point P4 with respect to the first rotation reference point P5 is opposite to the position of the rotation detection point P4 shown in FIG. 11A, as shown in FIG. 11C.

Figure 12A:
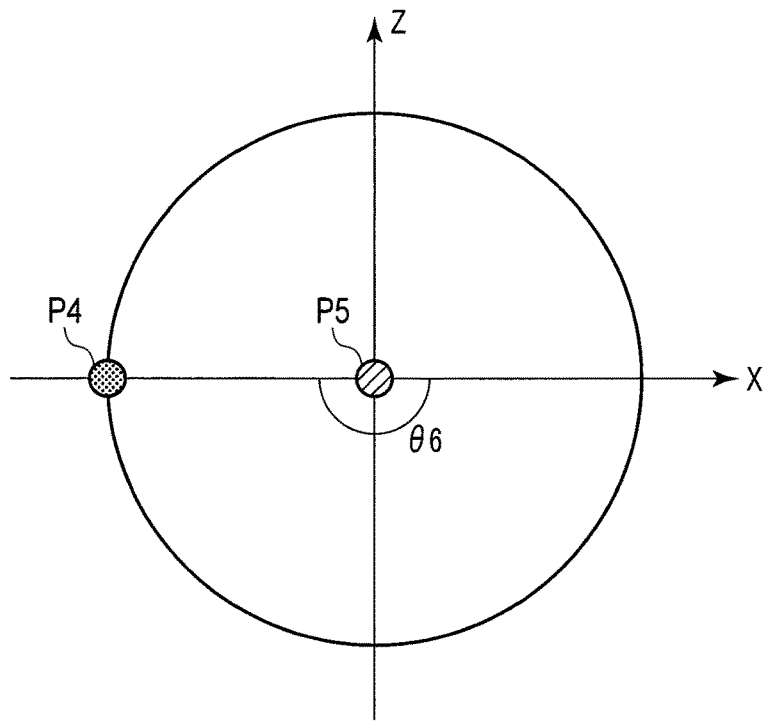
FIG. 12A is a diagram of the position relationship between the first rotation detection point and the first rotation reference point shown in FIG. 11A, as viewed on an X-Z plane with the first rotation reference point set as an original point.
Figure 12B:
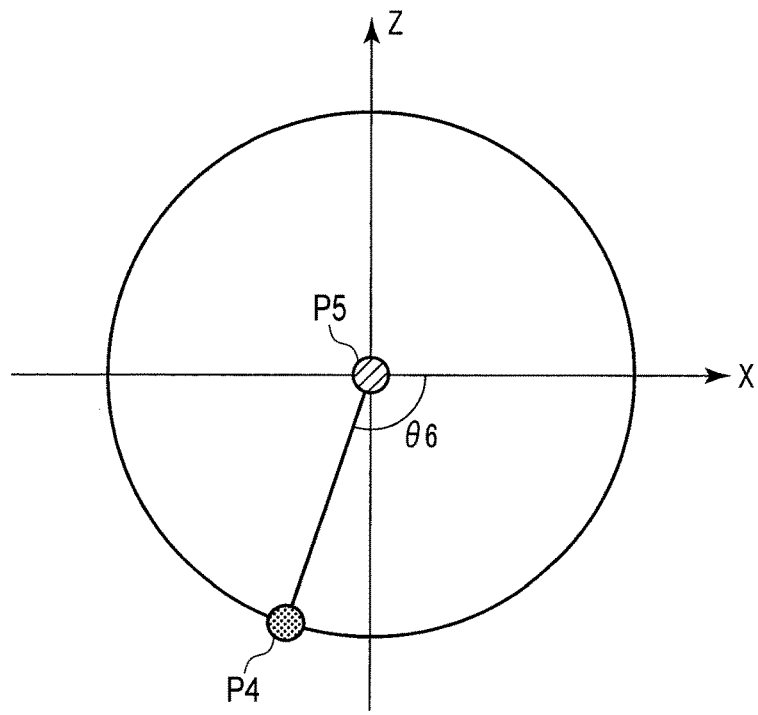
FIG. 12B is a diagram of the position relationship between the first rotation detection point and the first rotation reference point shown in FIG. 11B, as viewed on the X-Z plane with the first rotation reference point set as an original point.
Figure 12C:
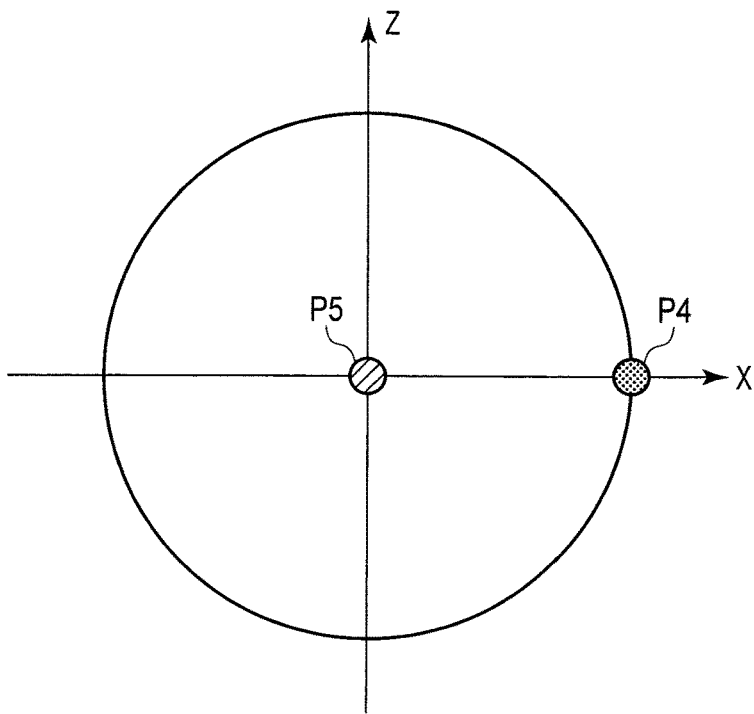
FIG. 12C is a diagram of the position relationship between the first rotation detection point and the first rotation reference point shown in FIG. 11C, as viewed on the X-Z plane with the first rotation reference point set as an original point.

FIGS. 12A, 12B, and 12C correspond to FIGS. 11A, 11B, and 11C, respectively, and show the positional relationship between the first rotation reference point P5 and the rotation detection point P4, as viewed on the X-Z plane with the first rotation reference point P5 as an original point. When the insertion section 30 rotates clockwise, the rotation detection point P4 rotates counterclockwise about the first rotation reference point P5. When the insertion section 30 rotates and changes to an N shape as shown in FIG. 11C, the position of the rotation detection point P4 is opposite to the position of the rotation detection point P4 shown in FIG. 12A, as shown in FIG. 12C. In this example, an axis formed by connecting the original point shown in FIG. 12C and the rotation detection point P4 shown in FIG. 12C, that is, the X-axis in the example shown in FIG. 12C is defined as a reference axis for calculating the lacked rotation quantity (hereinafter referred to as a "calculation reference axis"). The calculation reference axis may be calculated by the support information calculator 61 as an extension of the line connecting the rotation detection point P4 shown in FIG. 11A and the first rotation reference point P5 shown in FIG. 11A. The calculation reference axis is an axis that serves as a reference for calculating the rotation quantity of the insertion section 30. An angle that is formed between the calculation reference axis and the line connecting the rotation detection point P4 and the first rotation reference point P5 and is equal to or less than 180° is defined as "an angle θ6". As can be seen from FIGS. 12A, 12B, and 12C, when the angle θ6 becomes 0°, the rotation operation is ended, and the angle θ6 corresponds to the lacked rotation quantity.

Therefore, in the example 1, the support information calculator 61 calculates the rotation quantity of the insertion section 30 based on relative changes of a plurality of pieces of position information (position coordinates). The plurality of pieces of position information indicate the rotation detection point P4, the first rotation reference point P5, and the calculation reference axis. Specifically, the support information calculator 61 calculates the rotation quantity of the insertion section 30 based on the change of the angle θ6.

Next, the example 2 will be described.

As shown in FIG. 11A, the distance between the X-coordinate of the rotation detection point P4 and the X-coordinate of the first rotation reference point P5 is referred to as "AX". The distance AX serves as a reference for calculating the rotation quantity of the insertion section 30. A threshold for the distance AX is set in advance in the support information calculator 61. The threshold is stored in the storage section, and the support information calculator 61 may read the threshold from the storage section when performing the calculation.

In general, the insertion section 30 changes to an about linear shape by a removal operation after changing to the N shape shown in FIG. 11C. Therefore, the threshold is a value, for example, 30 mm, at which the insertion section 30 can be changed to an about linear shape by the removal operation.

The support information calculator 61 calculates the rotation quantity of the insertion section 30 based on the distance AX between the rotation detection point P4 and the first rotation reference point P5. Specifically, the support information calculator 61 calculates the lacked rotation quantity, that is, the rotation quantity of the insertion section 30 necessary for changing the state shown in FIG. 11A to the state shown in FIG. 11C based on the difference between the distance AX shown in FIG. 11A and the threshold. The lacked rotation quantity, which is represented by the distance AX in the example 2, and not by an angle about the longitudinal axis of the insertion section 30, can be used as an index.

The examples 1 and 2 show the distance AX on the X-Z plane and the X-coordinate, in other words, an example in which, during the rotation operation, the direction vector of the rotation detection point P4 is always oriented in the positive Y-axis direction (upward in the figures) and the direction vector of the first rotation reference point P5 is always oriented in the negative Y-axis direction (downward in the figures). However, the insertion section 30 may change its orientation inside the insertion target body in accordance with the insertion operation. Therefore, as in the first embodiment in which the rotation quantity of the insertion section 30 is calculated from the change of the direction vector information, a rotation calculation that causes the shape on the control section 40 side with respect to the first rotation reference point P5 to return to the original shape may be performed on the rotation detection point P4 and the first rotation reference point P5. By the rotation calculation, the direction vector of the rotation detection point P4 is oriented in the negative Y-direction, and the direction vector of the first rotation reference point P5 is oriented in the Y-axis direction. Operation support information indicates the rotation quantity of the insertion section 30 calculated based on the distance AX on the X-Z plane or the X-coordinate. Thereby, even if the shape of the insertion section 30 changes during the rotation operation, the calculation accuracy is improved.

Next, the example 3 will be described.

In the example 1, the support information calculator 61 calculates the lacked rotation quantity based on a plurality of pieces of position information; however, the present invention is not limited thereto. For example, the plurality of pieces of position information as the first information may include a second rotation reference point P8 arranged closer to the control section 40 than the first rotation reference point P5, as shown in FIGS. 13A, 13B, and 13C. For example, the X-coordinate of the second rotation reference point P8 is close to the X-coordinate of the first rotation reference point P5. The support information calculator 61 may calculate the rotation quantity of the insertion section 30 based on the position of the rotation detection point P4 with respect to a reference line L that is a straight line including the first rotation reference point P5 and the second rotation reference point P8, instead of the first rotation reference point P5.

The direction vector information may include a reference vector VB that corrects the rotation detection point P4 and serves as a reference. The reference vector VB is, for example, a direction vector of the first rotation reference point P5. The support information calculator 61 performs a rotation calculation that causes the reference vector VB after the rotation operation of the insertion section 30 to be oriented in the same direction as the reference vector VB before the rotation operation of the insertion section 30, on the rotation detection point P4. Then, the support information calculator 61 calculates the rotation quantity of the insertion section 30 based on the rotation detection point P4 rotated by the rotation calculation.

The reference line L or a vector may be used for the rotation detection point P4 side.

[Modification 3]

Hereinafter, a modification 3 of the present embodiment will be described. In the present modification, only the differences from the first embodiment will be described. In the present modification, description is provided by adopting a plurality of pieces of position information, specifically, a plurality of position coordinates as the first information.

Figure 14:
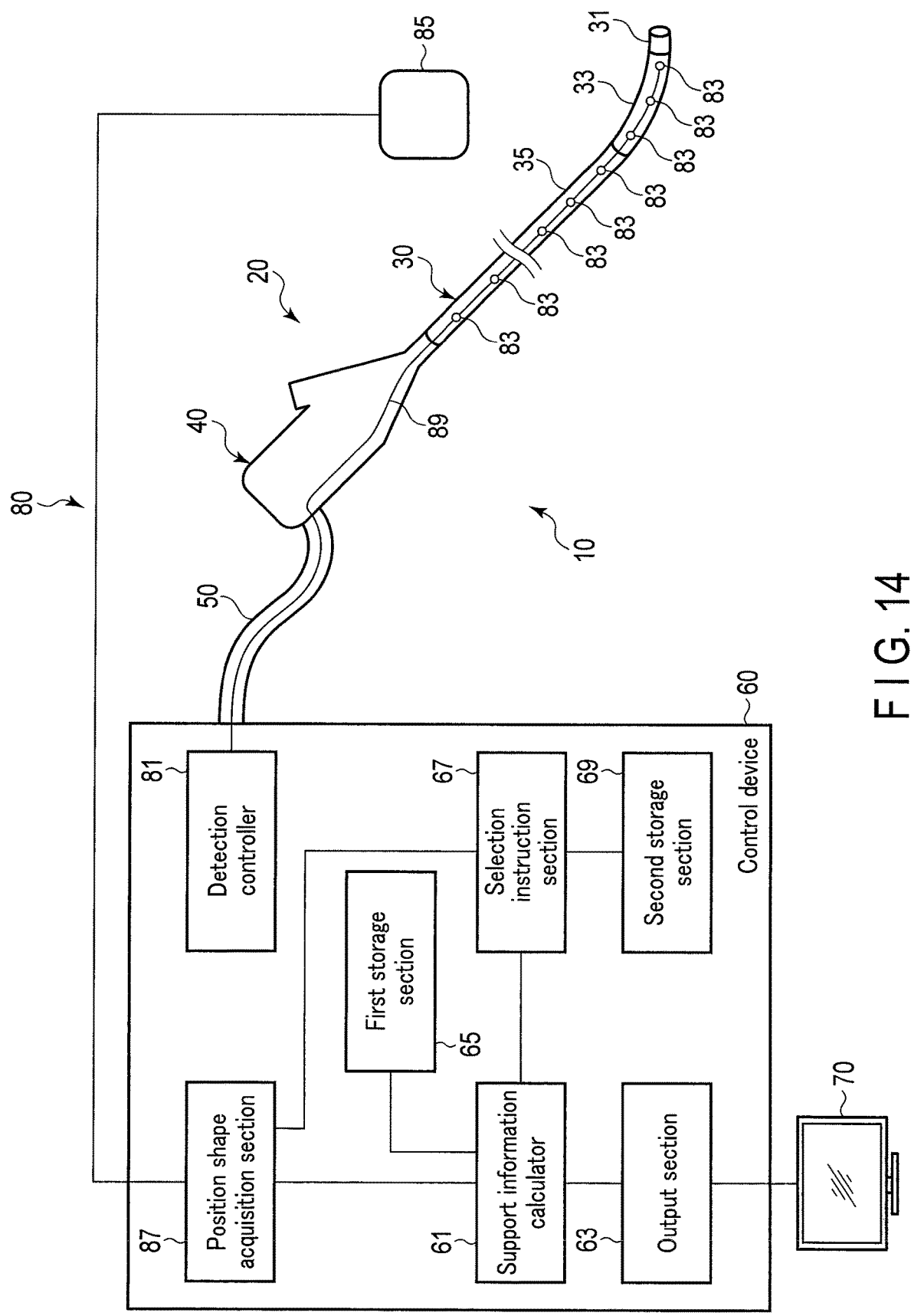
FIG. 14 is a schematic diagram of an insertion support system using a plurality of algorithms.

As shown in FIG. 14, the insertion support system 10 includes a first storage section 65 configured to store a plurality of algorithms including a certain algorithm used by the support information calculator 61 to calculate the rotation quantity of the insertion section 30. The first storage section 65 is disposed in the control device 60. For example, the plurality of algorithms includes a geometric calculation algorithm and a machine learning algorithm.

As described in the first embodiment and the modifications 1 and 2, the geometric calculation algorithm is an algorithm for geometrically calculating the rotation quantity of the insertion section 30 based on the first information that is at least one of the direction vector information of the insertion section 30 and the plurality of pieces of position information of the insertion section 30.

The machine learning algorithm is an algorithm that is constructed in advance by machine learning based on training data, which will be described later, and outputs the rotation quantity from at least one of the direction vector information of the insertion section 30 and the plurality of pieces of position information of the insertion section 30 (first information). The training data refers to a plurality of known data associating the rotation quantity of the insertion section 30 with at least one of the position information and the direction vector information. The training data is, for example, a large amount of data obtained by measuring the rotation quantity of the distal end of the insertion section 30 with respect to the Z-axis for various shapes of the insertion section 30. With the machine learning algorithm constructed using the training data, the support information calculator 61 can estimate a shape other than those related to the training data, that is, the relationship between a shape and a rotation quantity as a rotation quantity for an unknown shape.

The machine learning algorithm is usually constructed in advance before the insertion support system 10 is driven, and stored in the first storage section 65. During the driving of the insertion support system 10, the support information calculator 61 may create at least one of the direction vector information of the insertion section 30 and the plurality of pieces of position information of the insertion section 30, and data associated with the rotation quantity of the insertion section 30, that is, the training data, from a result of measuring the rotation quantity using the geometric calculation algorithm or other methods. Then, the first storage section 65 may store, as a machine learning algorithm, results derived by machine learning based on the training data created during driving of the insertion support system 10. Also, the machine learning algorithm may be reconstructed by adding the training data created during the driving of the insertion support system 10 to the already-constructed machine learning algorithm. In machine learning, the accuracy of the results derived by machine learning usually increases as the number of training data increases. Therefore, the support information calculator 61 can estimate the rotation quantity with higher accuracy by the machine learning algorithm reconstructed by adding the training data.

The support information calculator 61 of the present modification can access the first storage section 65. The support information calculator 61 calculates the rotation quantity of the insertion section 30 adopting an algorithm (geometric calculation algorithm or machine learning algorithm) from among a plurality of algorithms.

As described above, when the support information calculator 61 is configured by a processor, the first storage section 65 may function as an internal memory or an external memory (not shown) configured to be accessed by the processor.

The insertion support system 10 includes a selection instruction section 67 configured to select an algorithm to be used by the support information calculator 61 from among a plurality of algorithms, and instruct the support information calculator 61 to use the selected algorithm; and a second storage section 69 configured to store a plurality of training data that are referred to when the selection instruction section 67 selects an algorithm.

The selection instruction section 67 and the second storage section 69 are disposed in the control device 60. The selection instruction section 67 is configured by, for example, a hardware circuit including an ASIC. The selection instruction section 67 may be configured by a processor. When the selection instruction section 67 is configured by a processor, an internal memory or an external memory (not shown) configured to be accessed by the processor is arranged in the control device 60. The internal memory or the external memory stores a program code for causing the processor to serve as at least one of these functions when executed by the processor. The second storage section 69 may function as this memory.

The plurality of pieces of position information of the insertion section 30 and the direction vector information of the insertion section 30 acquired by the position shape acquisition section 87 are input to the support information calculator 61. Also, the plurality of pieces of position information of the insertion section 30 acquired by the position shape acquisition section 87 are input to the selection instruction section 67.

The selection instruction section 67 compares the position information input from the position shape acquisition section 87 with the training data stored in the second storage section 69, and determines the presence or absence of approximate training data of the position information acquired by the position shape acquisition section 87.

An example of the method of determining the presence or absence of the approximate training data will be described below.

The selection instruction section 67 calculates distances between a plurality of pieces of coordinate information that constitute position information acquired by the position shape acquisition section 87, and a plurality of pieces of coordinate information of the training data corresponding to the plurality of pieces of coordinate information that constitute position information acquired by the position shape acquisition section 87, and further calculates the sum of the distances calculated for each coordinate. That is, the selection instruction section 67 calculates the total difference between the position information acquired by the position shape acquisition section 87 and the position information of the training data. As the total difference is smaller, the selection instruction section 67 determines that the position information acquired by the position shape acquisition section 87 is the approximate training data. The selection instruction section 67 performs the above-described calculation on all pieces of coordinate information of the training data stored in the second storage section 69. Also, a threshold for the total distance is set in advance in the selection instruction section 67.

If there is training data indicating that the total distance is less than the threshold, the selection instruction section 67 determines that the training data close to the position information input from the position shape acquisition section 87 is stored in the second storage section 69. If the total distance is equal to or greater than the threshold for all the training data, the selection instruction section 67 determines that the training data close to the position information input from the position shape acquisition section 87 is not stored in the second storage section 69.

Let us assume that the rotation quantity of the insertion section 30 is calculated using a machine learning algorithm. The machine learning algorithm is an algorithm constructed based on training data. Therefore, if the position information input from the position shape acquisition section 87 is the same as or approximate to the training data, an error of the calculation result of the support information calculator 61 using the machine learning algorithm is small, and a high-precision calculation result can be expected. However, if the position information is greatly different from the training data, the error of the calculation result of the support information calculator 61 using the machine learning algorithm is highly likely to increase, and a high-precision calculation result cannot be expected.

If the training data that is the same as or approximate to the position information input from the position shape acquisition section 87 is stored in the second storage section 69, the error of the calculation result can be regarded as small even when a machine learning algorithm is used. Therefore, the selection instruction section 67 outputs an instruction to select a machine learning algorithm to the support information calculator 61.

On the other hand, if the training data close to the position information input from the position shape acquisition section 87 is not stored in the second storage section 69, the error of the calculation result is highly likely to increase when a machine learning algorithm is used. Therefore, the selection instruction section 67 outputs an instruction to select a geometric calculation algorithm to the support information calculator 61.

As described above, the selection instruction section 67 compares the first information with the training data, and selects a machine learning algorithm or a geometric calculation algorithm from among a plurality of algorithms based on the comparison result. Then, the selection instruction section 67 instructs the support information calculator 61 to calculate the rotation quantity using the selected algorithm. The support information calculator 61 accesses the first storage section 65, and uses the algorithm stored in the first storage section 65 in accordance with the instruction output from the selection instruction section 67 to calculate the rotation quantity of the insertion section 30 using the plurality of pieces of position information of the insertion section 30 and the direction vector information of the insertion section 30 stored in the first storage section 65.

In the above description, the method of selecting an algorithm is performed based on the comparison between the position information input from the position shape acquisition section 87 and the training data stored in the first storage section 65; however, other methods may be adopted for selecting an algorithm.

Other selection methods will be described below.

In deep learning, which is one type of machine learning, labeling of data is generally performed. For example, an element shown in image data is generally labeled. As a result, a label and a numerical value corresponding to the reliability of the label are output, as in "flower: 0.7," "tree: 0.2," "person: 0.1," for example. The labels in this example are "flower," "tree," and "person," and the photo of the flower has the highest reliability.

The rotation quantity (0° to 360°) has, for example, 36 labels in 10° increments (hereinafter referred to as "rotation quantity labels"). When deep learning is performed on the position information using the same method as described above, that is, when labeling is performed using a machine learning algorithm, the rotation quantity labels and the reliability thereof are output.

Next, the operation will be described.

First, the support information calculator 61 provisionally calculates the rotation quantity labels and the reliability thereof based on the input of the position information, as described above, by using a machine learning algorithm, and outputs the most reliable rotation quantity label and its reliability to the selection instruction section 67.

A threshold for the reliability is preset in the selection instruction section 67. The selection instruction section 67 compares the input reliability with the threshold. If the reliability is equal to or greater than the threshold, the selection instruction section 67 outputs an instruction to the support information calculator 61 so that the support information calculator 61 outputs the result of the rotation quantity label already calculated using the machine learning algorithm to the output section 63. If the reliability is equal to or lower than the threshold, the selection instruction section 67 determines that the reliability of the result of the machine learning algorithm is low. Then, the selection instruction section 67 outputs an instruction to the support information calculator 61 so that the support information calculator 61 selects a geometric calculation algorithm, calculates the rotation quantity, and outputs the calculation result to the output section 63.

The example in which the selection instruction section 67 selects a geometric calculation algorithm or a machine learning algorithm is shown; however, the present invention is not limited thereto. For example, depending on the intended use considering the calculation accuracy required, etc., or when sufficient learning is possible and the calculation accuracy by a machine learning algorithm is high for every position information, the support information calculator 61 may use only a machine learning algorithm. In this case, the selection instruction section 67 and the second storage section 69 are omitted.

Second Embodiment

Hereinafter, a second embodiment of the present invention will be described. In the present embodiment, only the differences from the first embodiment and the modifications of the first embodiment will be described.

Figure 15:
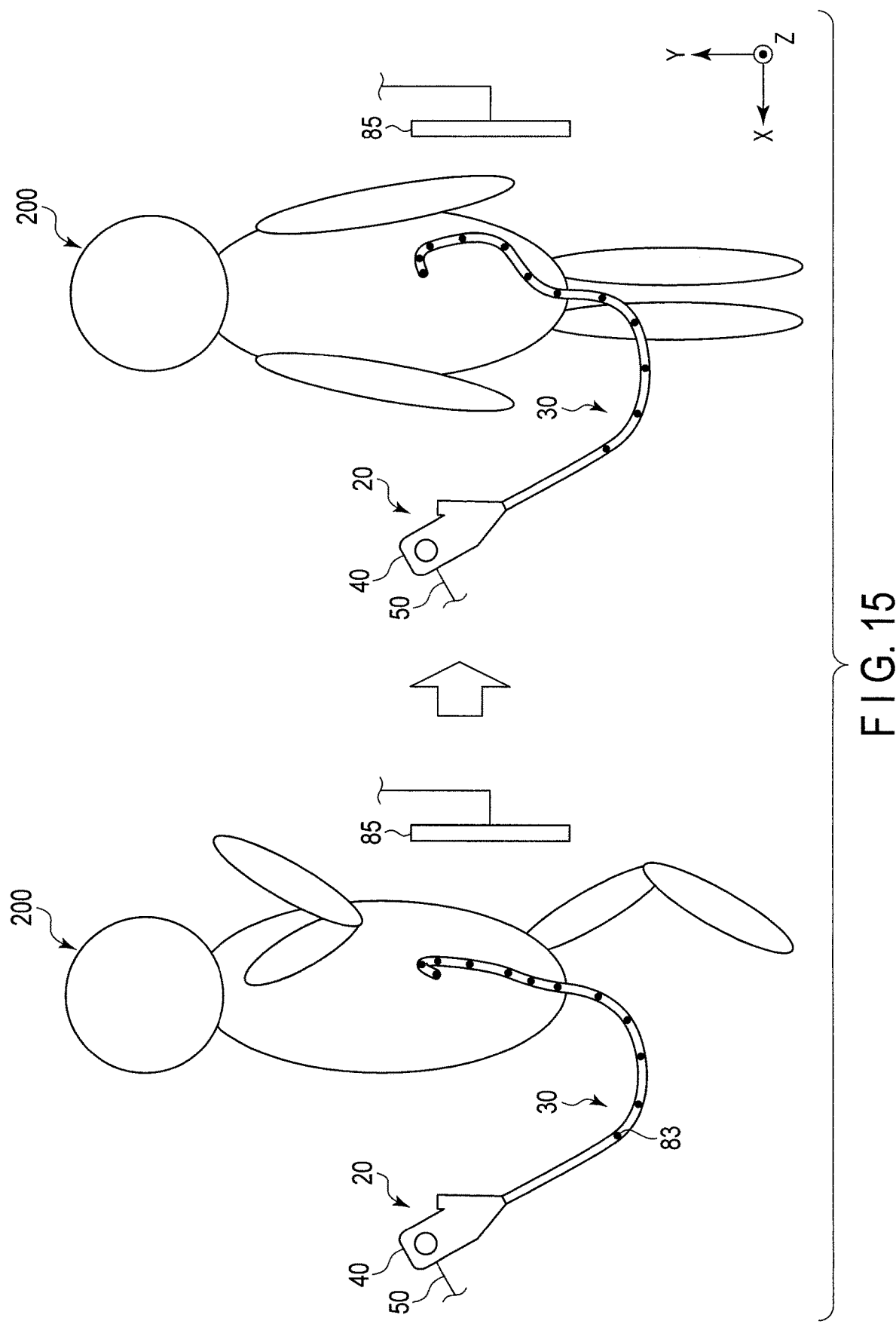
FIG. 15 is a diagram showing a postural change of an insertion target body.

As shown in FIG. 15, when the insertion section 30 is inserted into the large intestine, the insertion is generally performed, for example, in a left-side recumbent posture where an insertion target body 200 is lying sideways with the left side down. If it is difficult to perform the insertion in this left-side recumbent posture, the posture of the insertion target body 200 may be changed from the left-side recumbent posture to the supine position where the insertion target body 200 lies on his or her back. The postural change causes the shape of the insertion section 30 inserted into the large intestine to change due to the directional change of the gravity applied to the insertion target body 200 as a result of the postural change, and brings about an effect of improving the insertability of the insertion section 30.

In the postural change described below, the insertion target body 200 lying on the X-Y plane faces the Y-Z plane in the left-side recumbent posture and faces the XY-plane in the supine position.

The present embodiment is different from the first embodiment in that the support information calculator 61 calculates the postural change of the insertion target body 200 based on the rotation quantity of the insertion section 30 as the second information. In this embodiment, the calculation of the postural change indicates the rotation quantity of the insertion target body 200 associated with the postural change. The insertion section 30 also rotates along with the postural change. In the first place, when the posture is changed from the left-side recumbent posture to the supine position with the insertion section 30 inserted into the large intestine, the insertion section 30, where the magnetic field generator 83 is disposed, also rotates relative to the magnetic field detector 85. Therefore, the support information calculator 61 can calculate the postural change of the insertion target body 200 based on the rotation quantity of the insertion section 30 as the second information.

Hereinafter, the calculation of the postural change will be described.

Figure 16:
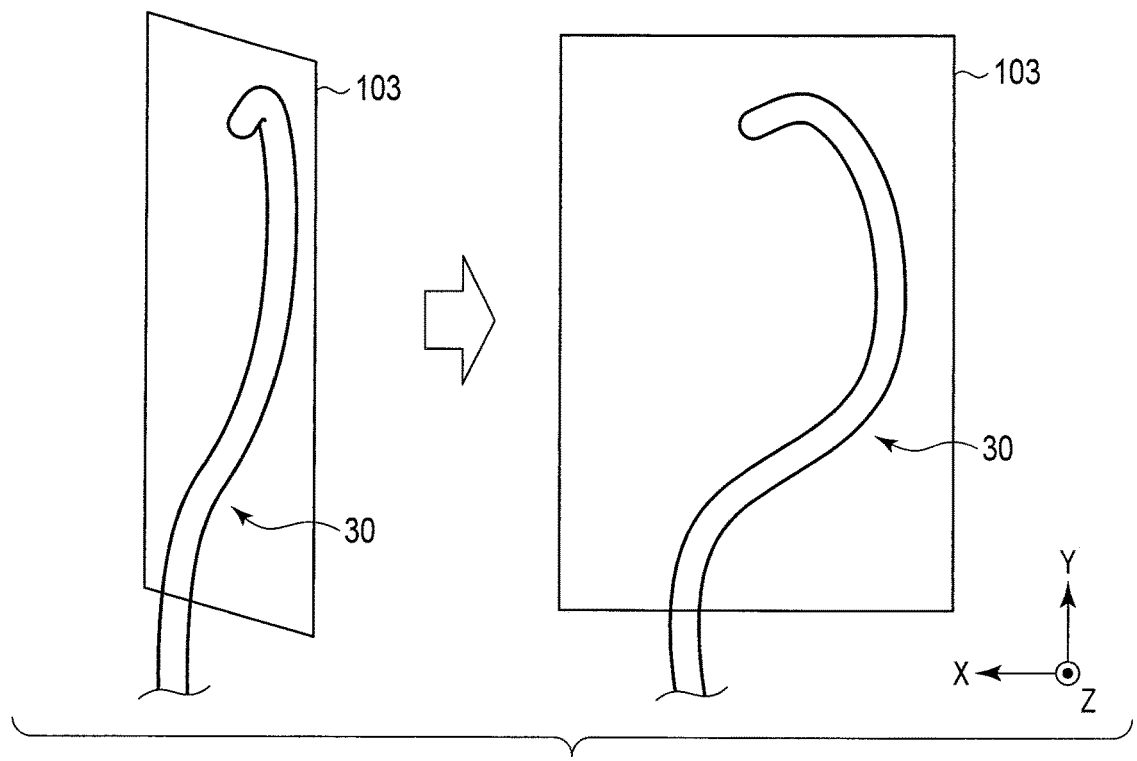
FIG. 16 is a diagram showing an insertion plane that is used to calculate the postural change.

As shown in FIG. 16, for example, the support information calculator 61 calculates a plane (hereinafter referred to as an "insertion plane 103") in the large intestine on which the insertion section 30 is placed, based on a plurality of pieces of position information (position coordinates) of the insertion section 30 inserted into the large intestine, as in the modification 1 of the first embodiment. The insertion plane 103 indicates a plane that approximates a plurality of pieces of position information (position coordinates), and is used to calculate the rotation quantity of the insertion section 30. The calculation of the insertion plane 103 can be performed by, for example, the commonly-known least-square method. In the present embodiment, every position information (position coordinate) of the insertion section 30 is used as the plurality of pieces of position information (position coordinates) of the insertion section 30 in order to improve the calculation accuracy. As in the modification 1 of the first embodiment, the support information calculator 61 calculates the rotation quantity of the insertion section 30 based on the insertion plane 103.

Although not shown in the figures, when the insertion section 30 is inserted into the large intestine in the left-side recumbent posture, the loop of the insertion section 30 spreads on a plane parallel to the Y-Z plane as a reference, and the insertion plane 103 is formed on the plane parallel to the Y-Z plane. When the support information calculator 61 calculates the postural change, the support information calculator 61 stores the initial position of the insertion plane 103 formed on the Y-Z plane, that is, the position coordinates of the insertion section 30 before rotation.

If the posture is not changed from the left-side recumbent posture to the supine position, and the insertion section 30 is rotated by the rotation operation of the insertion section 30 in the left-side recumbent posture, the entire insertion section 30 does not usually rotate due to a limited internal space of the insertion target body 200, and the insertion plane 103 also hardly tilts with respect to the Y-Z plane, remaining at an angle close to 0° with respect to the Y-Z plane. Under such circumstances, the support information calculator 61 calculates the rotation quantity of the insertion section 30 as the second information, and calculates, based on the result of this calculation, that the insertion plane 103 remains at an angle close to 0° with respect to the Y-Z plane. Then, the support information calculator 61 determines that the insertion plane 103 is not rotating based on the result of this calculation. Furthermore, the support information calculator 61 determines that the rotation operation is performed and that the postural change is not performed.

However, if the posture is changed from the left-side recumbent posture to the supine position, the entire insertion section 30 rotates along with the postural change, as shown in FIG. 15, and the insertion plane 103 also rotates from the Y-Z plane to the X-Y plane, for example, at an angle of approximately 90°, as shown in FIG. 16. Under such circumstances, the support information calculator 61 calculates the rotation quantity of the insertion section 30 as the second information, and calculates, based on the result of this calculation, that the insertion plane 103 has rotated from the Y-Z plane to the X-Y plane, for example, at an angle of approximately 90°. Then, the support information calculator 61 determines that the insertion plane 103 has rotated based on the result of this calculation. Furthermore, when the insertion plane 103 rotates, the support information calculator 61 determines that the rotation operation is not performed and that the postural change is performed. The support information calculator 61 calculates the rotation quantity of the insertion section 30 based on the change of the angle of the insertion plane 103 rotated by the postural change, and regards the calculated rotation quantity of the insertion section 30 as the rotation quantity of the insertion target body 200. The support information calculator 61 transmits the rotation quantity of the insertion section 30 and the rotation quantity of the insertion target body 200 to the output section 63. The output section 63 outputs the rotation quantity of the insertion section 30 and the rotation quantity of the insertion target body 200 to the display 70. Then, the display 70 displays the rotation quantity of the insertion section 30 and the rotation quantity of the insertion target body 200.

The determination may always be performed after the initial position is stored, or may be performed at a desired timing.

The support information calculator 61 may determine the type of posture based on the angle of the insertion plane 103 with respect to the Y-Z plane. Usually, due to the structure of the large intestine of the patient as the insertion target body 200, the loop of the insertion section 30 scarcely spreads in the direction of the patient's abdomen and back, and tends to spread in the direction from one flank toward the other flank of the patient or in the direction from the anus to the diaphragm of the patient. The wider the loop, the larger the insertion plane 103. Accordingly, the insertion plane 103 becomes larger in the direction from one flank toward the other flank of the patient or in the direction from the anus to the diaphragm of the patient. Therefore, if the angle of the insertion plane 103 with respect to the Y-Z plane is close to 0°, the support information calculator 61 determines that the posture is a left-side recumbent posture, and if the angle of the insertion plane 103 is close to 90°, the support information calculator 61 determines that the posture is a supine position.

Figure 17:
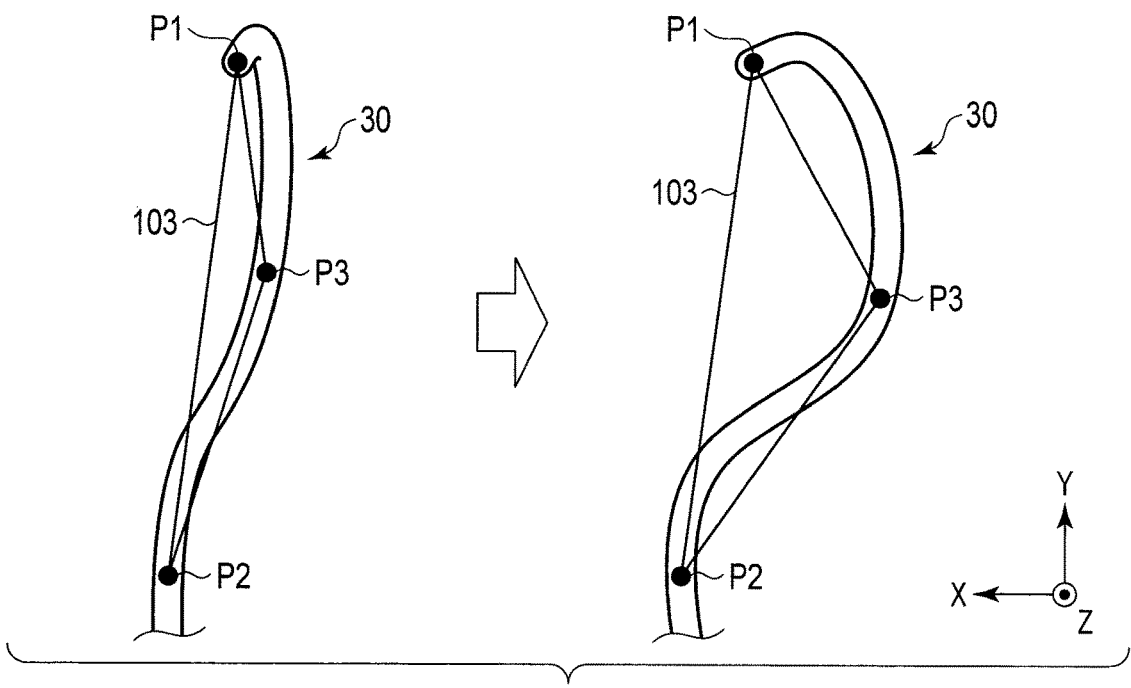
FIG. 17 is a diagram showing an example of the calculation for the insertion plane.

The plurality of pieces of position information (position coordinates) used to calculate the insertion plane 103 need not employ every position information (position coordinate) of the insertion section 30. For example, position information (position coordinates) of three points P1, P2, and P3 of the distal end, the proximal end, and the intermediate position between the distal end and the proximal end of the insertion section 30 may be used, as shown in FIG. 17. The support information calculator 61 calculates the insertion plane 103 on which they are arranged based on these pieces of position information (position coordinates). As the position information (position coordinates) used is reduced, the amount of calculation is reduced, and the load on the support information calculator 61 is reduced.

Next, an example of improving accuracy in determination of whether rotation of the insertion section 30 is caused by the rotation operation instead of the postural change or rotation of the insertion section 30 is caused by the postural change will be described.

In general, when the insertion section 30 is rotated by the postural change, the change of the shape of the insertion section 30 is small. However, when the insertion section 30 is rotated by the rotation operation, the change of the shape of the insertion section 30 is large. The determination in which accuracy is to be improved is focused on the shape change. First, the support information calculator 61 stores the position coordinates of the insertion section 30 before rotation, as shown by (A) in FIG. 18. Also, regardless of whether the insertion section 30 has been rotated by the rotation operation or rotated along with the postural change, the support information calculator 61 stores the position coordinates of the insertion section 30 after rotation and calculates the rotation quantity of the insertion section 30 as the second information, as shown by (B) in FIG. 18. The calculation may adopt the calculations described in the first embodiment and the modifications of the first embodiment.

Figure 18:
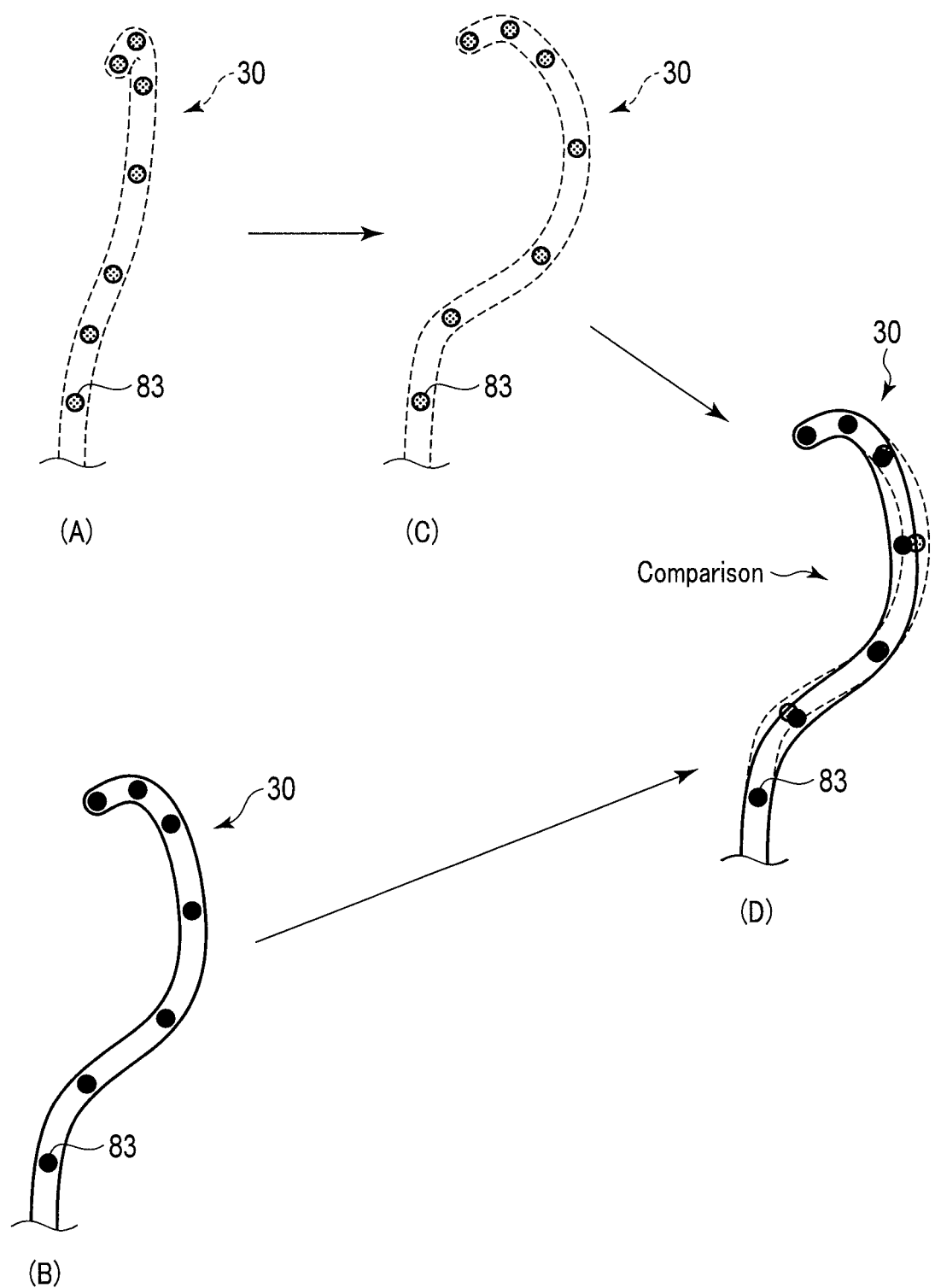
FIG. 18 is a diagram illustrating improvement of accuracy in determination of whether rotation of the insertion section is caused by a rotation operation instead of a postural change, or by a postural change.

As shown by (C) in FIG. 18, the support information calculator 61 performs a rotation calculation with the same amount as that of the rotation quantity of the insertion section 30 constituting the second information calculated by the support information calculator 61 on the position coordinates of the insertion section 30 before rotation shown by (A) in FIG. 18. That is, the support information calculator 61 performs, on the position coordinates of (A), a rotation calculation with the same amount as that of the rotation quantity for the position coordinates to change from (A) to (B). As a result, (C) is obtained. The position coordinates derived by the calculation are referred to as "virtual position coordinates". As described above, the support information calculator 61 performs a rotation calculation with the same amount as that of the rotation quantity being the second information on the position information of the insertion section 30 before or after rotation or on the direction vector information of the insertion section 30 before rotation.

Next, if the change of the position coordinates or direction vector information of the insertion section 30 before and after rotation is less than a threshold preset in the support information calculator 61, the support information calculator 61 determines that the posture has been changed. Also, if the change of the position coordinates or direction vector information of the insertion section 30 before and after rotation is equal to or greater than the threshold, the support information calculator 61 determines that the rotation operation has been performed. Specifically, the support information calculator 61 compares the virtual position coordinates with the actual position coordinates of the insertion section 30 after rotation, as shown by (D) in FIG. 18. In the comparison, the support information calculator 61, for example, calculates the sum of the distance differences with regard to the respective position coordinates. In general, when the insertion section 30 is rotated by the postural change, the change of the shape of the insertion section 30 is small. However, when the insertion section 30 is rotated by the rotation operation, the change of the shape of the insertion section 30 is large. Therefore, if the total distance of the position coordinates is less than the threshold, the support information calculator 61 determines that the insertion section 30 has been rotated by the postural change. If the total distance of the position coordinates is equal to or greater than the threshold, the support information calculator 61 determines that the insertion section 30 has been rotated by the rotation operation.

Figure 19:
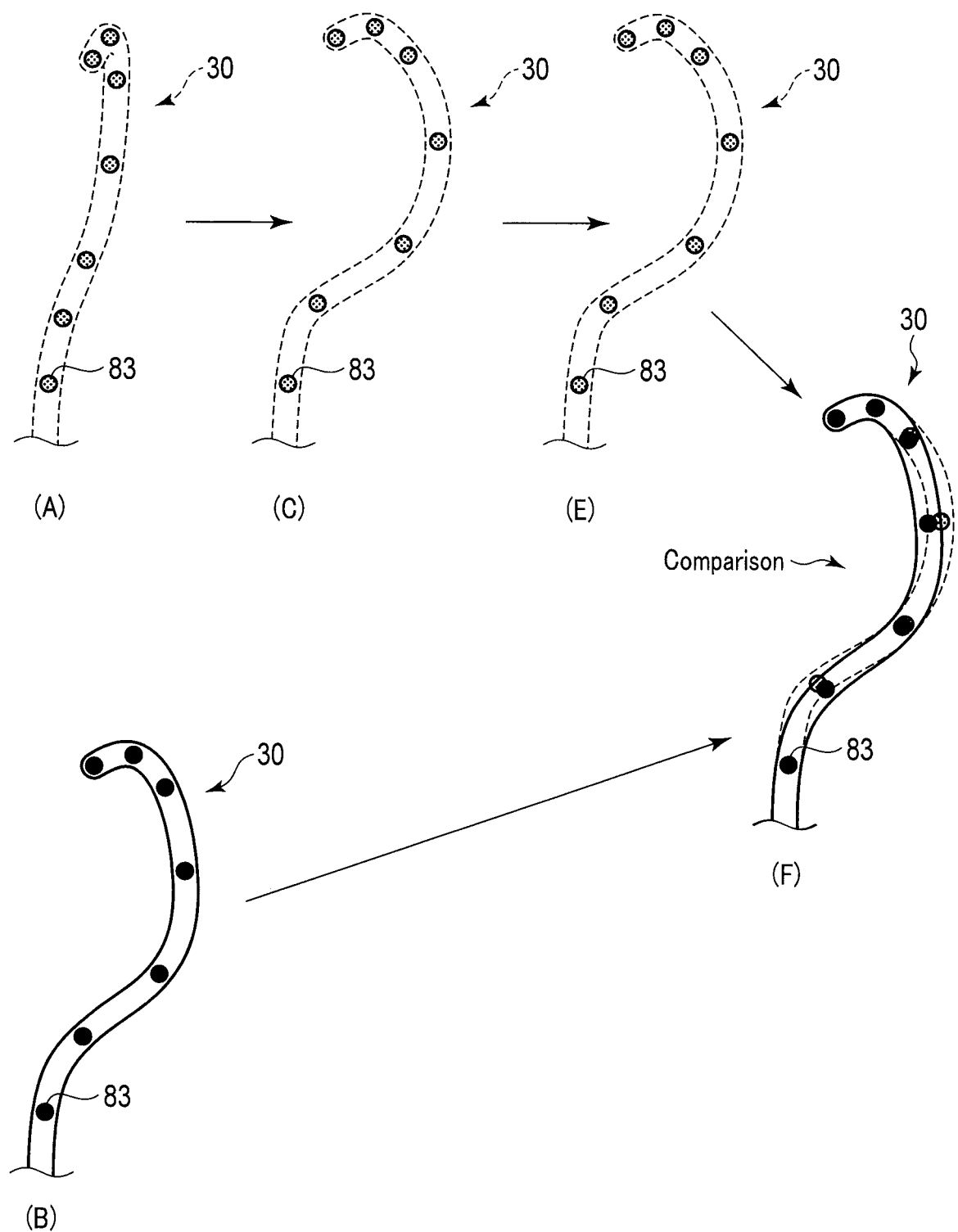
FIG. 19 is a diagram illustrating correction of a change of position coordinates caused by a change in the direction of gravity due to a postural change of the insertion target body.

In addition, when the posture is changed, the direction of gravity applied to the insertion target body 200 changes, resulting in the change of the shape of the insertion section 30 and the change of the position coordinates of the insertion section 30. The degree of the shape change and the coordinate change can be corrected based on the physical property values of the insertion section 30 such as the stiffness of the insertion section 30 and the weight of the insertion section 30. This correction will be described with reference to FIG. 19. The illustrations of (A), (B), and (C) in FIG. 19 are approximately the same as those of (A), (B), and (C) in FIG. 18. As shown by (E) in FIG. 19, the support information calculator 61 corrects, based on the physical property values, the change of the virtual position coordinates caused by the directional change of the gravity due to the postural change of the insertion target body 200. The support information calculator 61 may correct the change of the position coordinates by adjusting the threshold for the total distance of the position coordinates. Then, the support information calculator 61 compares the corrected position coordinates with the actual position coordinates of the insertion section 30 after rotation, as shown by (F) in FIG. 19. The comparison is approximately the same as the comparison in FIG. 18. Therefore, if the total distance of the position coordinates is less than the threshold, the support information calculator 61 determines that the insertion section 30 has been rotated by the postural change. If the total distance of the position coordinates is equal to or greater than the threshold, the support information calculator 61 determines that the insertion section 30 has been rotated by the rotation operation. Such correction enables the support information calculator 61 to perform more accurate determination.

Next, another example of improving the accuracy in the determination will be described.

The support information calculator 61 may make the determination based on the position coordinates of the insertion section 30 near the anus, which is an entrance to the inside of the insertion target body 200.

Although not shown in the figures, when the postural change is not performed and the rotation operation is performed on the insertion section 30, the position coordinates of the insertion section 30 near the anus usually hardly change. However, when the posture is changed, the position coordinates of the insertion section 30 near the anus shift in the X-direction or the Z-direction, as shown in FIG. 20. Therefore, a threshold is preset in the support information calculator 61 for the change of the position coordinates of the insertion section 30 near the anus. If the coordinate change is equal to or greater than the threshold, the support information calculator 61 determines that the insertion section 30 has been rotated by the postural change. If the coordinate change is less than the threshold, the support information calculator 61 determines that the insertion section 30 has been rotated by the rotation operation. As described above, if the change of the position coordinates of the insertion section 30 before and after rotation in the vicinity of the entrance of the insertion target body 200 is equal to or greater than the threshold, the support information calculator 61 determines that the posture has been changed. If the change of the position coordinates of the insertion section 30 before and after rotation in the vicinity of the entrance of the insertion target body 200 is less than the threshold, the support information calculator 61 determines that the rotation operation has been performed.

In the above description, the coordinates are used; however, the same applies to the direction vector information. Therefore, the support information calculator 61 corrects the vector of the insertion section 30 before rotation based on the second information. If the change of the direction vector information of the insertion section 30 before and after rotation is less than the threshold, the support information calculator 61 determines that the posture has been changed. The support information calculator 61 corrects, based on the physical property values, the change of the direction vector information caused by the directional change of gravity due to the postural change of the insertion target body 200.

In the present embodiment, the insertion plane 103 of the insertion section 30 is calculated, and the same calculation as that of the rotation of the insertion section 30 is performed based on the insertion plane 103. Also, in the present embodiment, the postural change can be calculated based on the rotation quantity of the insertion section 30.

The same calculation as that of the rotation quantity of the insertion section 30 that has already been calculated is performed on the position coordinates of the insertion section 30 before rotation. By comparing the virtual position coordinates with the actual position coordinates of the insertion section 30 after rotation, it is possible to improve the accuracy in the determination of whether the rotation is caused by the postural change or by the rotation operation.

Furthermore, even if the shape of the insertion section 30 is changed when the direction of gravity is changed by the postural change, the determination accuracy can be improved by correcting the shape change.

In addition, the determination accuracy can be improved by determining the change of the position coordinates of the insertion near the anus based on the threshold.

The present invention is not limited to the above embodiments, and can be modified in various manners in practice when implementing the invention without departing from the gist of the invention. Moreover, each of the embodiments may be implemented by being suitably combined to a maximum extent, in which case a combined effect will be obtained. Furthermore, the above embodiments include inventions at various stages, and various inventions can be extracted by an appropriate combination of a plurality of disclosed constituent elements.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion support system comprising:
a controller comprising hardware, the controller being configured to:
calculate second information related to a rotation quantity of the insertion section based on first information, the first information comprising at least one of: a plurality of pieces of position information related to a plurality of positions of an insertion section to be inserted into an insertion target body; and a plurality of pieces of direction vector information in a longitudinal axis direction of the insertion section and the rotation quantity being a twist quantity about a longitudinal axis of the insertion section; and
output the second information;
wherein the controller is configured to calculate a rotation detection plane based on the first information, and calculate the rotation quantity of the insertion section based on a change of an angle of the rotation detection plane before and after rotation;
the first information includes the direction vector information, and the direction vector information includes a reference vector for the rotation detection plane; and
the controller is configured to perform a rotation calculation that causes the reference vector after the rotation operation to be oriented in the same direction as the reference vector before the rotation operation, on the rotation detection plane after a rotation operation of the insertion section, and to calculate the rotation quantity of the insertion section based on a change of an angle of the rotation detection plane rotated by the rotation calculation performed on the rotation detection plane after the rotation operation.

2. The insertion support system according to claim 1, wherein the first information used to calculate the rotation detection plane is a plurality of pieces of position information of a curved portion of the insertion section having a curvature equal to or greater than a certain value.

3. An insertion support system comprising:
a controller comprising hardware, the controller being configured to:
calculate second information related to a rotation quantity of the insertion section based on first information, the first information comprising at least one of: a plurality of pieces of position information related to a plurality of positions of an insertion section to be inserted into an insertion target body; and a plurality of pieces of direction vector information in a longitudinal axis direction of the insertion section and the rotation quantity being a twist quantity about a longitudinal axis of the insertion section; and
output the second information;
wherein:
the first information is a plurality of pieces of position information of the insertion section;
the controller is configured to calculate the rotation quantity of the insertion section based on a relative change of the plurality of pieces of position information;
the plurality of pieces of position information include a rotation detection point for detecting rotation, and a first rotation reference point serving as a reference for the rotation;
the controller is configured to calculate the rotation quantity of the insertion section based on a distance between the rotation detection point and the first rotation reference point;
the controller includes a threshold for the distance between the rotation detection point and the first rotation reference point, the threshold serving as a reference for calculating the rotation quantity of the insertion section; and
the controller is configured to calculate the rotation quantity of the insertion section based on a difference between the distance and the threshold.

4. An insertion support system comprising:
a controller comprising hardware, the controller being configured to:
calculate second information related to a rotation quantity of the insertion section based on first information, the first information comprising at least one of: a plurality of pieces of position information related to a plurality of positions of an insertion section to be inserted into an insertion target body; and a plurality of pieces of direction vector information in a longitudinal axis direction of the insertion section and the rotation quantity being a twist quantity about a longitudinal axis of the insertion section; and
output the second information;
wherein:
the first information is a plurality of pieces of position information of the insertion section;
the controller is configured to calculate the rotation quantity of the insertion section based on a relative change of the plurality of pieces of position information;

the plurality of pieces of position information include a rotation detection point for detecting rotation, a first rotation reference point serving as a reference for the rotation, and a calculation reference axis serving as a reference for calculating the rotation quantity of the insertion section;

the controller is configured to calculate the rotation quantity of the insertion section based on a change of an angle formed between the calculation reference axis and a line connecting the rotation detection point and the first rotation reference point;

the first information comprises the plurality of pieces of position information and the direction vector information;

the direction vector information includes a reference vector that corrects the rotation detection point and serves as a reference; and the controller is configured to perform a rotation calculation that causes the reference vector after a rotation operation of the insertion section to be oriented in the same direction as the reference vector before the rotation operation of the insertion section, on the rotation detection point, and to calculate the rotation quantity of the insertion section based on the rotation detection point rotated by the rotation calculation.

5. An insertion support system comprising:
a controller comprising hardware, the controller being configured to:
calculate second information related to a rotation quantity of the insertion section based on first information, the first information comprising at least one of: a plurality of pieces of position information related to a plurality of positions of an insertion section to be inserted into an insertion target body; and a plurality of pieces of direction vector information in a longitudinal axis direction of the insertion section and the rotation quantity being a twist quantity about a longitudinal axis of the insertion section; and
output the second information;
wherein
the controller is configured to calculate the rotation quantity of the insertion section using the first information and an algorithm among a plurality of algorithms that include a machine learning algorithm constructed in advance by machine learning based on training data, the training data being a plurality of data associated with the rotation quantity of the insertion section;
the plurality of algorithms further include a geometric calculation algorithm for geometrically calculating the rotation quantity of the insertion section based on the first information;
the insertion support system further comprises a storage configured to store the plurality of algorithms, and
the controller is further configured to select the algorithm from among the plurality of algorithms and to use the selected algorithm; and
the controller is further configured to compare the first information with the training data, and to select the algorithm from among the plurality of algorithms based on a result of the comparison.

6. The insertion support system according to claim 1, wherein the controller is configured to calculate a change of a posture of the insertion target body based on the second information.

7. The insertion support system according to claim 6, wherein the controller is configured to:
perform a rotation calculation with the same amount as that of the rotation quantity constituting the second information on the position information of the insertion section before or after rotation, or on the direction vector information as the first information of the insertion section before rotation; and
determine that the posture has been changed if a change of the position information of the insertion section or a change of the direction vector information of the insertion section before and after rotation is less than a threshold.

8. An insertion support system comprising:
a controller comprising hardware, the controller being configured to:
calculate second information related to a rotation quantity of the insertion section based on first information, the first information comprising at least one of: a plurality of pieces of position information related to a plurality of positions of an insertion section to be inserted into an insertion target body; and a plurality of pieces of direction vector information in a longitudinal axis direction of the insertion section and the rotation quantity being a twist quantity about a longitudinal axis of the insertion section; and
output the second information;
wherein
the controller is further configured to:
calculate a change of a posture of the insertion target body based on the second information;
perform a rotation calculation with the same amount as that of the rotation quantity constituting the second information on the position information of the insertion section before or after rotation, or on the direction vector information as the first information of the insertion section before rotation;
determine that the posture has been changed if a change of the position information of the insertion section or a change of the direction vector information of the insertion section before and after rotation is less than a threshold; and
correct the change of the position information or the change of the direction vector information caused by a directional change of gravity due to the change of the posture of the insertion target body.

9. An insertion support system comprising:
a controller comprising hardware, the controller being configured to:
calculate second information related to a rotation quantity of the insertion section based on first information, the first information comprising at least one of: a plurality of pieces of position information related to a plurality of positions of an insertion section to be inserted into an insertion target body; and a plurality of pieces of direction vector information in a longitudinal axis direction of the insertion section and the rotation quantity being a twist quantity about a longitudinal axis of the insertion section; and
output the second information;
wherein
the controller is configured to:
calculate a change of a posture of the insertion target body based on the second information
determine that the posture has been changed if the change of the position information of the insertion section before and after rotation near an entrance of the insertion target body is equal to or greater than a threshold.

10. The insertion support system according to claim 1, further comprising a state acquisition apparatus for acquiring the first information, the state acquisition apparatus comprises:
- a magnetic field generator configured to generate a magnetic field;
- a magnetic field detector configured to detect an intensity of the magnetic field generated from the magnetic field generator; and
- the controller is configured to acquire the first information based on a result of the detection of the magnetic field detector,
- the magnetic field generator or the magnetic field detector is more than one, one of the magnetic field generator or the magnetic field detector being disposed inside the insertion section and disposed at different positions in the longitudinal axis direction of the insertion section, and
- an other of the magnetic field generator or the magnetic field detector is disposed outside the insertion section and fixed in place.

\* \* \* \* \*